US010905062B2

(12) United States Patent
Jackson

(10) Patent No.: US 10,905,062 B2
(45) Date of Patent: Feb. 2, 2021

(54) HIGH PROTEIN OAT SPECIES

(71) Applicant: General Mills, Inc., Minneapolis, MN (US)

(72) Inventor: Eric Wayne Jackson, Wamego, KS (US)

(73) Assignee: General Mills, Inc., Minneapolis, MN (US)

( * ) Notice: Subject to any disclaimer, the term of this patent is extended or adjusted under 35 U.S.C. 154(b) by 61 days.

(21) Appl. No.: 14/886,238

(22) Filed: Oct. 19, 2015

(65) Prior Publication Data

US 2017/0105379 A1  Apr. 20, 2017

(51) Int. Cl.
*A01H 5/10* (2018.01)
*A01H 6/46* (2018.01)

(52) U.S. Cl.
CPC ..................... *A01H 5/10* (2013.01)

(58) Field of Classification Search
None
See application file for complete search history.

(56) References Cited

U.S. PATENT DOCUMENTS

| | | | | |
|---|---|---|---|---|
| 5,620,692 A | * | 4/1997 | Potter | A61K 8/922 424/401 |
| 5,773,269 A | | 6/1998 | Somers et al. | |
| 8,574,644 B2 | | 11/2013 | Chatel et al. | |
| 8,697,956 B1 | | 4/2014 | Helms | |

OTHER PUBLICATIONS

Oliver et al, 2011, Theor. Appl. Genet., 123:1159-1171.*
Peterson et al, 2005, Crop Sci., 45:1249-1255.*
Ladizinsky, 1995, Theor. Appl. Genet., 91:639-646.*
Saidi et al, 2013, American Journal of Research Communication, 1:126-135.*
Ladizinsky,2014, "Development of Protein Rich Tetraploid Oat—Current State and Prospects", the Hebrew University of Jerusalem Israel, p. 1-12.*
Germeier et al., "*Report of a Working Group on Avena*", European Cooperative Programme for Plant Genetic Resources, Sixth Meeting, Oct. 19-22, 2010.
Ladizinsky, "*Development of Protein Rich Tetraploid Oat—Current State and Prospects*", the Hebrew University of Jerusalem Israel, Jul. 2014.
Universität Mainz, "*New DNA Test Identifies Ingredients in Foods*", Science Daily, Retrieved from the Internet htts://www.sciencedaily.com/releases/2013/03/130327092739.htm.
Hagberg, "*A Genetic Source used in Oat Improvement*", 3$^{rd}$ International Oar Conference, Lund, Sweden, Jul. 4-8, 1988.

* cited by examiner

*Primary Examiner* — Jason Deveau Rosen
(74) *Attorney, Agent, or Firm* — Diederiks & Whitelaw, PLC; Annette M. Frawley, Esq.; Rachel A. Kahler

(57) ABSTRACT

A high protein (up to 40%) tetraploid oat variety is provided that is suitable for large scale oat production using standard farming practices. A tetraploid oat variety includes one or more of lodging resistance, shattering resistance, erect growth habit, and seeds similar to traditional cultivated hexaploid oat, *A. sativa*. The tetraploid oat variety of the invention can also include a stable fatty acid profile, high iron content, high folic acid content, or high free essential amino acid content. A tetraploid oat variety may be used as foundational seed in a plant breeding program for development of lines and varieties with high protein content. Oat products produced from the tetraploid oat variety of the invention are also included as well as resultant oat foodstuffs such as high protein granola bars, hot cereals food stuffs, cold cereal foodstuffs, snackbars, cookies, gluten-free products, snacks, muffins, pancake mix and the like.

3 Claims, 5 Drawing Sheets

Specification includes a Sequence Listing.

SEQUENCE LISTING

```
<160> NUMBER OF SEQ ID NOS: 30

<210> SEQ ID NO 1
<211> LENGTH: 64
<212> TYPE: DNA
<213> ORGANISM: Avena magna

<400> SEQUENCE: 1
tgcagtccaa gatatttaat ggggaagtgt gcaatatcgc agccaaacag ggacttcacc      60
ctct                                                                  64

<210> SEQ ID NO 2
<211> LENGTH: 64
<212> TYPE: DNA
<213> ORGANISM: Avena magna

<400> SEQUENCE: 2
tgcagtccaa gatatttaat ggggaagtgt gcaatatcgc agccaaacag ggacttcatc      60
ctct                                                                  64

<210> SEQ ID NO 3
<211> LENGTH: 64
<212> TYPE: DNA
<213> ORGANISM: Avena magna

<400> SEQUENCE: 3
tgcagggctt gcctgaacat cccagaaccg cagggcacac ctatggcttc ggcacacgcc      60
gcca                                                                  64

<210> SEQ ID NO 4
<211> LENGTH: 64
<212> TYPE: DNA
<213> ORGANISM: Avena magna

<400> SEQUENCE: 4
tgcagggctt gcctgaacat cccagaaccg cggggcacac ctatggcttc ggcacacgcc      60
gcca                                                                  64

<210> SEQ ID NO 5
<211> LENGTH: 64
<212> TYPE: DNA
<213> ORGANISM: Avena magna

<400> SEQUENCE: 5
tgcagcagct cgaggcggac atgtcaatgt cgtgctccga gatcggaaga gcggttcagc      60
agga                                                                  64

<210> SEQ ID NO 6
<211> LENGTH: 64
```

```
<212> TYPE: DNA
<213> ORGANISM: Avena magna

<400> SEQUENCE: 6
tgcagcagct cgtggcggac atgtcaatgt cgtgctccga gatcggaaga gcggttcagc    60
agga                                                                 64

<210> SEQ ID NO 7
<211> LENGTH: 64
<212> TYPE: DNA
<213> ORGANISM: Avena magna

<400> SEQUENCE: 7
tgcagcgttg gacactaaag gagatacagt tgtgaatgct aataagaaaa gtcagcttc     60 catc                                                                 64

<210> SEQ ID NO 8
<211> LENGTH: 64
<212> TYPE: DNA
<213> ORGANISM: Avena magna

<400> SEQUENCE: 8
tgcagcgttg gacagtaaag gagatacagt tgtgaatgct aataagaaaa gtcagcttc     60 catc                                                                 64

<210> SEQ ID NO 9
<211> LENGTH: 64
<212> TYPE: DNA
<213> ORGANISM: Avena magna

<400> SEQUENCE: 9
tgcaggatcg ccacgtcgac ggtctccgcc atggaccgca ccgagatcgg aagagcggtt    60
cagc                                                                 64

<210> SEQ ID NO 10
<211> LENGTH: 64
<212> TYPE: DNA
<213> ORGANISM: Avena magna

<400> SEQUENCE: 10
tgcaggctcg ccacgtcgac ggtctccgcc atggaccgca ccgagatcgg aagagcggtt    60
cagc                                                                 64

<210> SEQ ID NO 11
<211> LENGTH: 64
<212> TYPE: DNA
<213> ORGANISM: Avena magna

<400> SEQUENCE: 11
tgcagcggct cgacatcagt gacaacgagc tctctggcgc attccccgcc aacgtgtctc    60
tccc                                                                 64

<210> SEQ ID NO 12
<211> LENGTH: 64
<212> TYPE: DNA
<213> ORGANISM: Avena magna

<400> SEQUENCE: 12
tgcagcggct cgacatcagt gacaacgagc tctctggcgc gttccccgcc aacgtgtctc    60
```

```
tccc                                                              64
```

<210> SEQ ID NO 13
<211> LENGTH: 64
<212> TYPE: DNA
<213> ORGANISM: Avena magna

<400> SEQUENCE: 13

```
tgcaggtcga accgcagcgg gaactcgtag tcggcatcac acaccatctc ccagctccgc  60
atca                                                              64
```

<210> SEQ ID NO 14
<211> LENGTH: 64
<212> TYPE: DNA
<213> ORGANISM: Avena magna

<400> SEQUENCE: 14

```
tgcaggtcga accgcagcgg gaactcgtag tcggcgtcac acaccatctc ccagctccgc  60
atca                                                              64
```

<210> SEQ ID NO 15
<211> LENGTH: 64
<212> TYPE: DNA
<213> ORGANISM: Avena magna

<400> SEQUENCE: 15

```
tgcagccatg cccgccgcga atgcaaacgg gaatcacaga ttccaatcaa caaaccagag  60
aaat                                                              64
```

<210> SEQ ID NO 16
<211> LENGTH: 64
<212> TYPE: DNA
<213> ORGANISM: Avena magna

<400> SEQUENCE: 16

```
tgcagccatg cccgccgcga atgcaaacgg gaatcacaga ttccaatcaa caaaccagag  60
caat                                                              64
```

<210> SEQ ID NO 17
<211> LENGTH: 64
<212> TYPE: DNA
<213> ORGANISM: Avena magna

<400> SEQUENCE: 17

```
tgcagaagca ccgcagcaag caagcttcgc taatgcttac gctcggatcg gatgaggcca  60
agca                                                              64
```

<210> SEQ ID NO 18
<211> LENGTH: 64
<212> TYPE: DNA
<213> ORGANISM: Avena magna

<400> SEQUENCE: 18

```
tgcagaagca ccgcagcaag caagcttcgc taatgcttac ggtcggatcg gatgaggcca  60
agca                                                              64
```

<210> SEQ ID NO 19
<211> LENGTH: 64
<212> TYPE: DNA
<213> ORGANISM: Avena magna

```
<400> SEQUENCE: 19
tgcaggacct cgacctcagc gccaactacc tctacggcgc cgtcccgaga tcggaagagc    60
ggtt                                                                 64

<210> SEQ ID NO 20
<211> LENGTH: 64
<212> TYPE: DNA
<213> ORGANISM: Avena magna

<400> SEQUENCE: 20
tgcaggacct cgacctcggc gccaactacc tctacggcgc cgtcccgaga tcggaagagc    60
ggtt                                                                 64

<210> SEQ ID NO 21
<211> LENGTH: 64
<212> TYPE: DNA
<213> ORGANISM: Avena magna

<400> SEQUENCE: 21
tgcagacaca aaggcatggg tacgacgagc cccgacagca accgcacgtc cgcatggagg    60
gtac                                                                 64

<210> SEQ ID NO 22
<211> LENGTH: 64
<212> TYPE: DNA
<213> ORGANISM: Avena magna

<400> SEQUENCE: 22
tgcagacaca aaggcatggg tacgacgagc ctcgacagca accgcacgtc cgcatggagg    60
gtac                                                                 64

<210> SEQ ID NO 23
<211> LENGTH: 64
<212> TYPE: DNA
<213> ORGANISM: Avena magna

<400> SEQUENCE: 23
tgcagttagg tagcacagct agctgttctt attttgccca acactttttt ctattggccg    60
agat                                                                 64

<210> SEQ ID NO 24
<211> LENGTH: 64
<212> TYPE: DNA
<213> ORGANISM: Avena magna

<400> SEQUENCE: 24
tgcagttagg tagcacagct agctgttctt attttgccca acatttttt ctattggccg     60 agat                                                                 64

<210> SEQ ID NO 25
<211> LENGTH: 64
<212> TYPE: DNA
<213> ORGANISM: Avena magna

<400> SEQUENCE: 25
tgcagttttg gagaatattt cagttttcaa aaccacagta tttattgcat acaaatacct    60
caaa                                                                 64
```

```
<210> SEQ ID NO 26
<211> LENGTH: 64
<212> TYPE: DNA
<213> ORGANISM: Avena magna

<400> SEQUENCE: 26
tgcagttttg gagaatattt cagttttcaa aaccacagta tttattgcat ccaaatacct      60
caaa                                                                   64

<210> SEQ ID NO 27
<211> LENGTH: 64
<212> TYPE: DNA
<213> ORGANISM: Avena magna

<400> SEQUENCE: 27
tgcagcacca gcagcaccac cagctggacg agacgcagca gagctggctg ctcggcccgc      60
cgag                                                                   64

<210> SEQ ID NO 28
<211> LENGTH: 64
<212> TYPE: DNA
<213> ORGANISM: Avena magna

<400> SEQUENCE: 28
tgcagcacca gcagcaccac cagctggacg agacgcagca gagctggctg ctgggcccgc      60
cgag                                                                   64

<210> SEQ ID NO 29
<211> LENGTH: 64
<212> TYPE: DNA
<213> ORGANISM: Avena magna

<400> SEQUENCE: 29
tgcagaagga caggctacgt gacttaacaa acaagggatg caacttgtta ccttgattga      60
actt                                                                   64

<210> SEQ ID NO 30
<211> LENGTH: 64
<212> TYPE: DNA
<213> ORGANISM: Avena magna

<400> SEQUENCE: 30
tgcagaagga caggctacgt ggcttaacaa acaagggatg caacttgtta ccttgattga      60
actt                                                                   64
```

HIGH PROTEIN OAT SPECIES

FIELD OF THE INVENTION

The invention relates to oat breeding, and a new domesticated tetraploid oat species having high protein content. Methods of developing cultivars and varieties of this species, specific lines, uses and products derived therefrom are also disclosed.

BACKGROUND OF THE INVENTION

Protein is an essential part of the human diet and crops containing a complete amino acid profile are scarce. Common cultivated cereal grains, a staple food source in most of the countries of the world, are primarily rich in starch and fiber (soluble and insoluble). Unfortunately, these grains have modest levels of grain protein (~10%) and few contain all the amino acids required in the human diet. Common cultivated oat (*Avena sativa*) has long been a healthy food and ingredient primarily due to favorable levels of grain beta glucan (soluble fiber), antioxidants, and a beneficial fatty acid profile. For decades, oat has been widely favored as an ingredient in cold/hot cereals and snack bars. Oats include ten to fifteen species in genera *Avena*. All oats have edible seeds, though they are small and hard to harvest in most species. The most important cultivated species of oats are common oat (*Avena sativa*), Abyssinian oat (*Avena abyssinica*), naked or hulless oats (*Avena nuda*), and lopsided oat (*Avena strigosa*).

Attempts have been made to increase the protein levels in cultivated oat to make oat-based food products a premium amino acid source. Little gain has been made in this endeavor only increasing levels of grain protein from ~10-15% to ~20%. *Avena magna*, a wild relative of cultivated oat, is a promising source of protein. However, the lack of favorable agronomic characteristics (e.g., cultivation and harvestability) have limited the use of *A. magna* as a crop. Prior attempts to domesticate this wild species by crossing with *A. sativa*, either to transfer traits from *A. magna* to *A. sativa* or transfer traits from *A. sativa* to *A. magna*, have failed to produce a cultivatable oat plant that retains the favorable nutritional qualities of wild *A. magna*.

SUMMARY OF THE INVENTION

Applicants have spent significant time breeding and selecting *A. magna* for domestication traits. Despite its favorable high protein content, high iron content, good taste and fatty acid distribution, the wild oat species has proven difficult to impossible to domesticate for large scale production. With its tetraploid nature, there was concern that the wild variety may not even possess the genetic material for cultivation traits. Wild tetraploid (four sets of chromosomes) *A. magna* plants are not amenable to standard mechanical farming practices. The plants are very tall and lodge, growing flat on the ground. Seeds are hairy and difficult to hull, plugging traditional hullers, see FIG. 1. Applicant has successfully domesticated this tetraploid species, which allows for mechanical planting, harvesting and milling. Applicant has further developed lines and varieties for use in breeding the oat species of the invention. The varieties remain tetraploid, in distinction from *A. sativa*, which is hexaploid, or having six sets of chromosomes (AA, CC and DD genomes; 2n=6x=42), and have good cultivation traits. Lines developed by Applicants through years of traditional breeding techniques have superior agronomics compared to wild *A. magna*, but maintain desirable grain protein levels and fatty acid distribution profiles.

Provided herein is a plant of a tetraploid oat variety that is cultivatable using one or more standard farming practices. Standard farming practices can include mechanical planting, mechanical harvesting, and/or mechanical milling. In some embodiments, a plant of a tetraploid oat variety that is cultivatable using one or more standard farming practices can be *Avena magna*. In some embodiments, the tetraploid oat variety that is cultivatable using one or more standard farming practices is 96.5.6, 96.5.34, 96.5.55, or 100.2.35, or a descendant thereof. A tetraploid oat variety provided herein can have one or more of the following traits being comparable or superior to *Avena sativa* variety 'Leggett': stature, shattering resistance, lodging resistance, plant height, time to maturity, ease of dehulling, and seed yield.

In some embodiments, a plant of a tetraploid oat variety that is cultivatable using one or more standard farming practices can have a seed protein content of greater than 14% or greater than 18%, a seed oleic/linoleic ratio greater than 1, a seed oleic/linoleic ratio that is superior to that of *A. sativa* 'Leggett', a seed iron content that is superior to that of *A. sativa* 'Leggett', a seed folic acid content that is superior to that of *A. sativa* 'Leggett', a seed protein content that is superior to that of *A. sativa* 'Leggett', and/or a seed free essential amino acid content that is superior to that of *A. sativa* 'Leggett'.

Also provided herein is an oat plant produced from growing seed of a plant of a tetraploid oat variety that is cultivatable using one or more standard farming practices.

Also provided herein is a progeny of a plant of a tetraploid oat variety that is cultivatable using one or more standard farming practices, where the progeny is cultivatable using one or more standard farming practices. The progeny can have a lineage including a second oat plant. In some embodiments, a progeny of a plant of a tetraploid oat variety that is cultivatable using one or more standard farming practices can have a seed protein content of greater than 14% or greater than 18%, a seed oleic/linoleic ratio greater than 1, a seed oleic/linoleic ratio that is superior to that of *A. sativa* 'Leggett', a seed iron content that is superior to that of *A. sativa* 'Leggett', a seed folic acid content that is superior to that of *A. sativa* 'Leggett', a seed protein content that is superior to that of *A. sativa* 'Leggett', and/or a seed free essential amino acid content that is superior to that of *A. sativa* 'Leggett'.

An oat ingredient derived from a plant of a tetraploid oat variety that is cultivatable using one or more standard farming practices is provided herein. The oat ingredient can be included in a composition or a product.

Provided herein is an oat plant of an oat variety having a seed protein content greater than about 18%. In some embodiments, an oat plant of an oat variety having a seed protein content greater than about 18% is a tetraploid oat plant. In some embodiments, the oat plant is *A. magna*. In some embodiments, the oat variety is cultivatable using one or more standard farming techniques, such as mechanical planting, mechanical harvesting, and/or mechanical milling. In some embodiments, the oat variety is 96.5.6, 96.5.34, 96.5.55, or 100.2.35, or a descendant thereof.

In some embodiments, a plant of an oat variety having a seed protein content greater than about 18% can have a seed oleic/linoleic ratio greater than 1, a seed oleic/linoleic ratio that is superior to that of *A. sativa* 'Leggett', a seed iron content that is superior to that of *A. sativa* 'Leggett', a seed folic acid content that is superior to that of *A. sativa*

'Leggett', a seed protein content that is superior to that of *A. sativa* 'Leggett', and/or a seed free essential amino acid content that is superior to that of *A. sativa* 'Leggett' 0.26. In some embodiments, the variety has one or more of the following traits being comparable or superior to *A. sativa* 'Leggett': stature, shattering resistance, lodging resistance, plat height, time to maturity, ease of dehulling, and seed yield.

Also provided herein is a progeny plant of a plant of an oat variety having a seed protein content greater than about 18%, where the progeny is cultivatable using one or more standard farming practices. In some embodiments, the progeny has a seed protein content, a seed oleic/linoleic ratio, a seed iron content, a seed folic acid content, and/or a seed free essential amino acid content that is superior to that of *A. sativa* 'Leggett'. In some embodiments, the progeny has a lineage including a second oat plant.

An oat ingredient derived from a plant of an oat variety having a seed protein content of greater than about 18% is also provided. The oat ingredient can be included in a composition or a product.

Provided herein is a plant of the species *Avena magna* ssp *domestica*. In some embodiments, the *A. magna* ssp *domestica* plant is fertile with wild *Avena magna*. A population of plants including a plurality of *A. magna* ssp *domestica* plants is also provided.

DETAILED DESCRIPTION OF THE INVENTION

I. Introduction

Cultivated oat (*Avena sativa*) has long been known as a healthy food and ingredient primarily based on favorable levels of grain beta glucan (soluble fiber), antioxidants, and a beneficial fatty acid profile. Unfortunately, like other cereal grains, common cultivated oats typically have modest levels of grain protein (~10%).

Attempts have been made to increase the protein levels in cultivated oat so that common oat-based food products can become a premium amino acid source. However, little gain has been made in this endeavor, only increasing levels of grain protein from ~10-15% to ~20%. *Avena magna*, a wild relative of cultivated oat, is a promising source of protein. However, wild *A. magna* lacks favorable agronomic characteristics for cultivation. For example wild *Avena magna* oat plants are not amendable to mechanical harvesting because they lodge and shatter, and the seeds/grain are large and furry and clog traditional mechanical threshing and dehulling machines.

Other attempts of domesticating *A. magna* failed for a number of reasons. Because *A. magna* is tetraploid (having 4 sets of chromosomes) while domesticated *Avena sativa* is hexaploid (6 sets of chromosomes), it was believed that *A. magna* may lack the genes necessary to produce a variety with traits (e.g., shattering resistance, upright growth habit, and the like) that would make it suitable for cultivation using standard farming practices. Previous attempts to domesticate *A. magna* thus resorted in either introducing high protein content from *A. magna* into *A. sativa* or introducing domestication traits from *A. sativa* into *A. magna*, which resulted in largely sterile plants, plants that require female cytoplasm from a hexaploid *A. sativa* parent, plants that are hexaploids which do not retain the beneficial nutritional traits of wild *A. magna*, or tetraploid oat plants that have lost the high protein content of wild *A. magna*.

Figure 1:
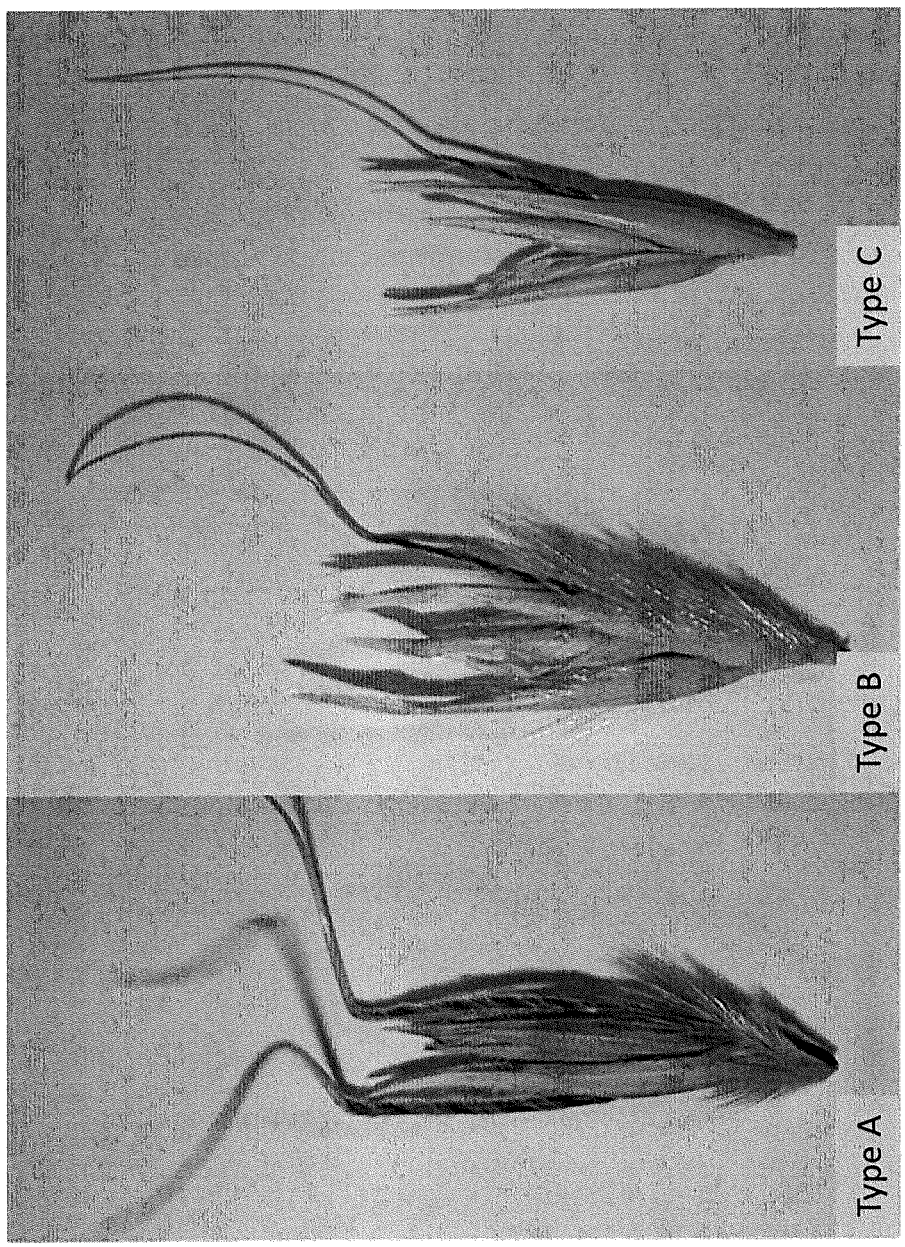
FIG. 1 includes photographs showing tetraploid oat (*Avena magna*) with varying levels of domestication. Intermediate domestication types were characterized by two articulate awns with dark glumes and basal pubescence (Type A), a single articulate awn with light glumes and reduced basal pubescence (Type B) and a single articulate awn with light glumes and no basal pubescence (Type C).
Figure 2:
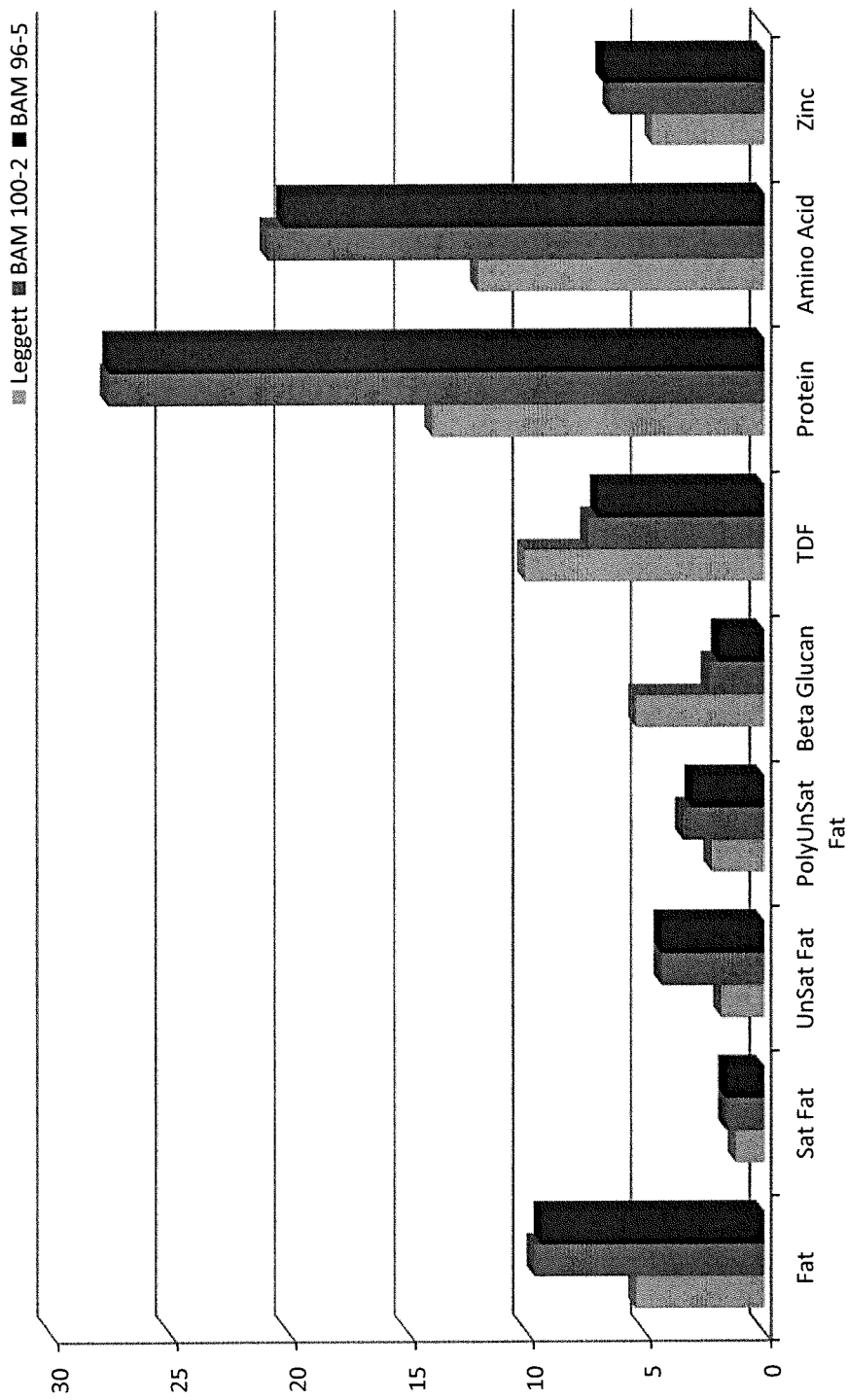
FIG. 2 is a graph showing the percentage of grain nutritional traits as measured in whole grain flour. *A. sativa* 'Leggett' was used as the hexaploid oat control to compare with two tetraploid oat lines (BAM 100-2 is Line 100.2 and BAM 96-5 is Line 96.5). All analytical measurements were performed at Medallion Lab in Minneapolis, Minn.

Using traditional plant breeding techniques, we succeeded in producing a new tetraploid oat variety that is cultivatable using one or more standard farming practices. Unlike past attempts at domestication of tetraploid oats, this stable and true to form tetraploid oat variety retains a high grain protein content similar to wild *A. magna*, containing at least 14% grain protein content (e.g., at least 18%, or between 28% to 40% grain protein content) (FIG. 2). In some embodiments, grain of a tetraploid oat variety provided herein has at least twice the levels of at least one amino acid (FIG. 3) when compared to *A. sativa*. These characteristics make *A. magna* a desirable grain for development of high quality protein products.

In addition, we have discovered a cultivatable tetraploid oat variety provided herein can have a grain fatty acid profile based on the linoleic (18:1) to linoleic (18:2) fatty acid ratio (FIG. 4) that is more stable against oxidation as compared to the fatty acid profile of *A. sativa*. A more stable fatty acid profile can impart the grain and products made from the grain of a tetraploid oat variety provided herein with an extended shelf life. In addition, reduced fatty acid oxidation can improve the flavor profile over the shelf life of the grain or products.

Thus, provided herein is a tetraploid oat variety having grain with one or more desirable nutritional qualities, such as high protein content and a stable fatty acid profile, and exhibiting characteristics making it suitable for cultivation using one or more standard farming practices. As used herein, the term "variety", also referred to herein as a "line," refers to a population of plants that are defined by the expression of characteristics resulting from a certain lineage or given genotype or combination of genotypes, distinguished from any other plant grouping by these characteristics and considered as a unit with regard to its suitability for being propagation unchanged. A variety is sufficiently homozygous and homogeneous to be used for commercial grain production or further breeding.

II. Nutrition

A tetraploid oat variety provided herein has a high seed protein content, with at least 15% (e.g., at least 18% or at least 22%) seed protein content. In some embodiments, a tetraploid oat variety has a seed protein content of from about 28% to about 40%. As used herein the term "protein content" includes the typical percentage by weight of protein in the oil free meal of the mature whole dried seeds. This can be determined by AOCS Official Method Ba 4e-93 Combustion Method for the Determination of Crude Protein. Also, protein could be analyzed using NIR (Near Infrared) spectroscopy as long as the instrument is calibrated according to the manufacturer's specifications, reference AOCS Procedure Am 1-92 Determination of Oil, Moisture and Volatile Matter, and Protein by Near-Infrared Reflectance. Generally moisture content of seed is normalized to 10% for reporting of protein content.

In some embodiments, a tetraploid oat variety has a seed protein content that is superior to $A.$ $sativa$ variety 'Leggett'. The term "superior" when comparing a tetraploid oat variety to $A.$ $sativa$ variety 'Leggett' herein means that the variety demonstrates a measurable improvement (e.g., a statistically significant improvement ($p<0.05$)) in a physiological, morphological or nutritional trait when compared to $A.$ $sativa$ 'Leggett'. The term "comparable" when comparing a tetraploid oat variety to $A.$ $sativa$ variety 'Leggett' herein means that the variety demonstrates a physiological, morphological or nutritional trait that is not significantly different (e.g., statistically significantly different ($p≥0.05$)) as compared to $A.$ $sativa$ variety 'Leggett'. Comparisons are made when grown under the same environment under the same conditions. An improvement in a trait includes for example, a more erect plant stature, a higher resistance to shattering demonstrated by less seed loss, a higher resistance to lodging demonstrated by fewer plants lodged, a shorter plant height, greater ease of dulling demonstrated by use of mechanical harvesting equipment, higher seed yield per acre, a higher folic acid seed content, a higher ratio of oleic acid content to linoleic acid content in seed, a higher seed iron content, a higher seed protein content, and a higher seed free essential amino acid content, a shorter time to maturity. Content of any specific component of seeds (such as iron, fatty acid, etc.) may be determined by any standard assay methods commonly used in the art.

In some embodiments, a tetraploid oat variety provided herein has a relatively stable fatty acid profile, based on the seed oleic fatty acid (18:1) to linoleic fatty acid (18:2) content ratio. The majority of the seed fatty acid content in oats is unsaturated (monounsaturated or polyunsaturated. However, monounsaturated fatty acids are more stable against oxidation than polyunsaturated fatty acids. An oleic fatty acid to linoleic fatty acid ratio that is higher is expected to be more stable against oxidation than a lower ratio. Oxidation of fatty acids can result in "off" or rancid flavors or odors, and can result in reduced shelf life of foods containing fatty acids.

In some embodiments, a tetraploid oat variety has an oleic to linoleic acid ratio that is superior to that of $A.$ $sativa$ variety 'Leggett'. For example, a tetraploid oat variety can have a ratio of linoleic (18:1) fatty acids to linoleic (18:2) fatty acids that is greater than 1 (e.g., greater than 1.1 or greater than 1.2).

In some embodiments, an oat ingredient derived from a tetraploid oat variety provided herein or a product containing an oat ingredient derived from a tetraploid oat variety provided herein can exhibit an increased shelf life, or an improved flavor or odor over the shelf life, of a similar oat ingredient or product containing an oat ingredient derived from $A.$ $sativa.$ In some embodiments, a tetraploid oat variety provided herein can have one or more additional nutritional characteristics, such as a seed iron content, seed folic acid content or seed free essential amino acid content, that are superior to that of $A.$ $sativa$ variety 'Leggett'.

III. Agronomic Traits

A tetraploid oat variety is cultivatable using one or more standard farming practices, which include practices involved in commercial crop production, such as mechanical planting (e.g., using a disc planter), mechanical harvesting (e.g., using a combine harvester), mechanical threshing, and mechanical dehulling, as opposed to hand planting, harvesting, threshing, dehulling, and the like. Characteristics of a tetraploid oat variety provided herein that make it amenable to cultivation using one or more standard farming practice include, without limitation, an upright habit, shattering resistance, lodging resistance, and seeds/grain similar in appearance and threshability to $A.$ $sativa.$ For example, described herein are 6 different lines of tetraploid oat exhibiting varying degrees of shattering resistance, lodging resistance, upright habit, and reduced seed pubescence (hairiness), with 4 lines that are highly shattering resistant, fully upright, highly lodging resistant, and have seeds that are almost visually indistinguishable from $A.$ $sativa.$ In some embodiments, a tetraploid oat variety provided herein can be mechanically dehulled with at least 50% efficiency (i.e., at least 50 seeds per 100 are removed from their hulls) using an oat dehulling machine, such as Model TFYM 1000 (Envirotextiles, LLC, Glenwood Springs, Colo., USA).

Surprisingly, a tetraploid oat variety provided herein can have one or more agronomic traits being comparable or superior to $A.$ $sativa$ variety 'Leggett'. For example, a tetraploid oat variety can have one or more of the following characteristics: semi-dwarf (e.g, a height at maturity of from about 120 cm to about 150 cm), early maturing (e.g., maturity until 50% flowering of about 110 days to about 120 days), or a similar groat weight to $A.$ $sativa$ variety 'Leggett' (e.g., from about 30 mg to about 50 mg). In some embodiments, a tetraploid oat variety can have a similar or greater seed yield to $A.$ $sativa$ variety 'Leggett'. For example, a tetraploid oat variety can have a similar number of seeds per panicle to $A.$ $sativa$ variety 'Leggett' (e.g., from 17 to 25 seeds per panicle), or have a similar or greater number of panicles per plant as $A.$ $sativa$ variety 'Leggett' (e.g., from about 4 to about 15 panicles per plant). A trait of a tetraploid oat variety can be considered superior to $A.$ $sativa$ variety 'Leggett' if it provides one or more advantage to, for example, planting, growing, harvesting, milling, and yield. For example, a higher yield or greater lodging resistance when plants are grown under the same conditions are considered superior traits.

IV. Genetics and Breeding

A tetraploid oat variety provided herein includes 28 chromosomes (e.g., CC and DD genomes, each with 7 pairs of chromosomes), in contrast to *A. sativa*, which is hexaploid (AA, CC, and DD genomes; 2n=6x=42 chromosomes). In addition, a tetraploid oat variety provided herein is fertile with itself or other tetraploid oat varieties and wild accessions via standard pollination techniques, and without the need for embryo rescue or other biotechnological techniques. A tetraploid oat variety provided herein can have greater than 50% allele sharing similarity (e.g., greater than 60% or greater than 70%) with *Avena magna* ssp *domestica* line 96.5.34, 96.5.6, or 100.2.235.

A plant of a tetraploid oat variety (e.g., *A. magna* ssp *domestica* line 96.5.34, 96.5.6, or 100.2.235) provided herein can serve as a parent in a genetic cross with a second oat plant to produce progeny. In some embodiments, such as when the second oat plant is a tetraploid oat plant, progeny of such a cross can be fertile. In some embodiments, such as when the second oat plant is not a tetraploid oat plant, progeny of such a cross can be infertile.

In some embodiments, a plant of a tetraploid oat variety provided herein can be used to develop additional oat varieties that are cultivatable using one or more standard farming practice. Additional oat varieties can be produced using any standard breeding technique, and can take advantage of the plant's method of pollination. Oat plants (*Avena* sp.), are recognized to be naturally self-pollinated plants which, while capable of undergoing cross-pollination, rarely do so in nature. Thus, control of pollination can be used to develop additional oat varieties.

A plant is self-pollinated if pollen from one flower is transferred to the same or another flower of the same plant. A plant is sib-pollinated when individuals within the same family or line are used for pollination. A plant is cross-pollinated if the pollen comes from a flower on a different plant from a different family or line. The term cross-pollination herein does not include self-pollination or sib-pollination.

A cross between two different homozygous lines produces a uniform population of hybrid plants that may be heterozygous for many gene loci. A cross of two heterozygous plants each that differ at a number of gene loci will produce a population of plants that differ genetically and will not be uniform. Regardless of parentage, plants that have been self-pollinated and selected for type for many generations become homozygous at almost all gene loci and produce a uniform population of true breeding progeny. The term "homozygous plant" is hereby defined as a plant with homozygous genes at 95% or more of its loci.

Choice of breeding or selection methods can depend on the mode of plant reproduction, heritability of the trait(s) being improved, and type of variety used commercially (e.g., F1 hybrid variety, pureline variety, etc.). A breeding program can include five or more generations of selection and breeding to obtain a population of plants with desired traits that are stably heritable. A breeding program can include any appropriate breeding technique or combination of breeding techniques. Known breeding techniques include, without limitation, pedigree breeding, backcross breeding, single seed descent, bulk breeding. Breeding programs typically include a periodic, objective evaluation of the efficiency of the breeding procedure. Evaluation criteria vary depending on the goal and objectives, but can include gain from selection per year based on comparisons to an appropriate standard, overall value of the advanced breeding lines, and number of successful varieties produced per unit of input (e.g., per year, per dollar expended, etc.).

In addition, methods such as outcrossing to wild populations, mutation induction, or transgene introduction, can be used for introducing genetic variability during one or more breeding step. Such methods can be used to introduce new traits, such as disease resistance or tolerance to various environmental conditions (e.g., drought), or improve existing traits.

Selection of plants for each generation of breeding can be based on one or more criteria, including phenotypic and/or genotypic traits. Phenotypic traits can be used to select one or more parent plants for breeding by examining physical and/or biochemical characteristics. For example, plants having an upright habit and/or possessing a seed protein content of greater than 15% can be selected for use in a breeding program at one or more stage of the breeding program. Additional phenotypic traits can include seed yield, head configuration, glume configuration, seed configuration, lodging resistance, disease resistance, plant height, rate of maturity, and the like.

Genotypic traits can be identified using one or more molecular markers in marker-assisted selection. Marker-assisted selection can use one or more techniques, such as Starch Gel Electrophoresis, Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), and Single Nucleotide Polymorphisms (SNPs) may be used in plant breeding methods. One use of molecular markers is Quantitative Trait Loci (QTL) mapping. QTL mapping identifies molecular markers, which are known to be closely linked to alleles that have measurable effects on a phenotypic trait.

For highly heritable traits, a choice of superior individual plants evaluated at a single location can be effective, whereas for traits with low heritability, selection may be based on mean values obtained from replicated evaluations of families of related plants. Popular selection methods commonly include pedigree selection, modified pedigree selection, mass selection, and recurrent selection.

Also provided herein is a descendant of *A. magna* ssp *domestica* line 96.5.34, 96.5.6, or 100.2.235. A descendant of *A. magna* ssp *domestica* line 96.5.34, 96.5.6, or 100.2.235 is cultivatable using one or more standard farming practices and can retain one or more traits exhibited by *A. magna* ssp *domestica* line 96.5.34, 96.5.6, or 100.2.235, such as protein content greater than 15%, a ratio of linoleic (18:1) fatty acids to linoleic (18:2) fatty acids that is greater than 1, or the like.

Another embodiment of the invention is an essentially derived variety of *A. magna* ssp *domestica* line 96.5.34, 96.5.6, or 100.2.235 or a locus conversion of *A. magna* ssp *domestica* line 96.5.34, 96.5.6, or 100.2.235. As determined by the UPOV Convention, essentially derived varieties may be obtained for example by the selection of a natural or induced mutant, or of a somaclonal variant, the selection of a variant individual from plants of the initial variety, backcrossing, or transformation by genetic engineering. An essentially derived variety of *A. magna* ssp *domestica* line 96.5.34, 96.5.6, or 100.2.235 is further defined as one whose production requires the repeated use of *A. magna* ssp *domes-*

*tica* line 96.5.34, 96.5.6, or 100.2.235 or is predominately derived from *A. magna* ssp *domestica* line 96.5.34, 96.5.6, or 100.2.235. International Convention for the Protection of New Varieties of Plants, as amended on Mar. 19, 1991, Chapter V, Article 14, Section 5(c). A locus conversion refers to plants within a variety that have been modified in a manner that retains the overall genetics of the variety and further comprises one or more loci with a specific desired trait, such as male sterility, insect, disease or herbicide resistance. Examples of single locus conversions include mutant genes, transgenes and native traits finely mapped to a single locus. One or more locus conversion traits may be introduced into a single oat variety.

V. Processing, Ingredients and Products

After harvest, oat grains can be processed in preparation for making an oat ingredient, or a composition or product containing an oat ingredient. Processing steps can include, without limitation drying, cleaning, sizing or grading, dehulling, steaming, or kilning.

An oat ingredient derived from a tetraploid oat variety that is cultivatable using one or more standard farming practices, or a composition or product comprising such an oat ingredient, can have one or more benefit over an oat ingredient derived from *A. sativa* (or composition or product containing such an ingredient). For example, an oat ingredient derived from a tetraploid oat variety can have a higher protein content, a longer shelf life, a higher iron content, or a higher folic acid content than an oat ingredient derived from *A. sativa*. In some embodiments, a composition or product comprising an oat ingredient derived from a tetraploid oat variety provided herein can have a benefit of providing a desired protein content, shelf life, iron content, or folic acid content without the need, or with reduced need, of other ingredients traditionally used to supplement such nutritional and shelf life benefits, such as soy protein, antioxidants, and inorganic iron supplements.

An oat ingredient is "derived" from an oat plant by milling, purifying, isolating, extracting or other production methods applied to the plants of the invention. The term "plant" as used herein refers to whole plants, plant parts (e.g., pollen, ovule, tissues such as leaves, stems, flowers, roots, seed), cultured or uncultured plant cells (e.g., callus) and progeny of same. The term "plant" refers to plants of any variety of ploidy levels, including polyploid, diploid, haploid and hemizygous. Examples of oat ingredients include but are not limited to oat oil extract, oat flour, oat groats, steel-cut oats, rolled oats, quick oats, oat bran, or individual components thereof.

A composition comprising an oat ingredient includes a mixture incorporating one or more oat ingredients provided herein. Examples of compositions comprising an oat ingredient include but are not limited to a flour mix, a pre-mix, dough, and the like.

An oat ingredient can be included in a product. A "product" with reference to a composition comprising an oat ingredient includes any of a number of consumer products made from oat ingredients, or compositions comprising oat ingredients such as granola, muesli, granola bars, hot cereal food stuffs, cold cereal foodstuffs, snackbars, cookies, gluten-free products, snacks, muffins, pasta, pancake mix, dairy substitute, animal feed, or any other product which employs the use of an oat ingredient. In some embodiments, an oat ingredient provided herein can be included in an animal feed or animal feed supplement to increase the amount of at least one nutrient (e.g., protein or iron) in the milk of a milk producing animal fed the animal feed or animal feed supplement.

EXAMPLES

Example 1—Tetraploid Oat Line Agronomic Traits

Several tetraploid oat lines were developed displaying one or more traits suitable for cultivation using one or more standard farming practices. *Avena magna* ssp *domestica* lines designated 96.5.6, 96.5.34, 96.5.55, and 100.2.235 display spring habit with erect growth and short stature (≤91.0 cm). Plants head in early-to-mid season and are resistant to lodging and shattering. Stems contain dense green-to-dark green board (≥1.6 mm, penultimate) leaves with erect angles and terminate with long (≥27.0 cm) broad (≥17.8 cm) equilateral panicles. The panicles have a straight hairless rachis that is highly branched and produces abundant spikelets (≥18.0). The spikelets are white-to-yellow in color and display basal semi-abscission without scars or hairs. Spikelets contain an average of two fertile florets (≤3.8% sterility) with long (≥2.8 mm) glumes that are yellow in color. Spikelets for lines 96.5.6 and 96.5.34 contain yellow hairless lemma, while 100.2.235 lemmas are yellow-to-gray and glabose. Awns are normally absent and are non-twisted when they do occur on the lemma. Seed is similar to cultivated oat (*A. sativa*, 2n=6x=42, AACCDD) and appears white-to-yellow in color with absence of basal hair and marginal pubescence. Groats are easily separated from the glumes via mechanical separation with an efficiency of approximately 65% and are plump (≥2.54 cm L and ≥0.64 cm W) with a mean 1,000 kernel weight of 30.3 g. Nutrient profile of the grain is highlighted by an average of tocopherols (vitamin E), and 9.1% (DV) oil of which 49.6% (DV) is oleic acid (18:0) to 37.2% (DV) linoleic acid (18:1). The total grain fiber is 8.5% (DV) of which 2.9% (DV) is beta glucan and 1.0% (DV) resistant starch.

Table 1 below shows the total seed, groat percentage and shattering comparisons among several cultivatable tetraploid oat lines. Lines 96.5.6, 96.5.55, 100.2.235 and 96.5.34 all have good shattering resistance, high groat percentage and high seed yield in pounds as compared to parental lines 96.5 and 100.2. Lines 100.2.231 and 100.2.233 have a moderate seed yield and high groat percentage as compared to parental lines 96.5 and 100.2.

TABLE 1

Yield, groat, and shattering comparisons

| Line | Total Seed Amount (lbs) | Groat (%) | Shattering (0-4) |
| --- | --- | --- | --- |
| 96.5.6 | 4.2 | 70.0 | 1.0 |
| 96.5.34 | 5.0 | 70.0 | 1.0 |
| 96.5.55 | 4.1 | 70.0 | 1.0 |
| 100.2.231 | 1.5 | 70.0 | 4.0 |
| 100.2.233 | 1.2 | 60.0 | 4.0 |
| 100.2.235 | 3.9 | 70.0 | 1.0 |
| 96.5 | NA | 32.0* | 4.0 |
| 100.2 | NA | 20.0* | 4.0 |

Table 2 shows various trait observations of various cultivatable tetraploid oat lines. Lines 100.2.235, 96.5.34 and 96.5.6 are stable for the described traits reported over different years and locations.

TABLE 2

Traits Across Tetraploid Oat lines

| Line_ID | Awn No. | Glume Length (mm) | Habit (0 = prostrate; 1 = erect) | Head Category | Leaf Density | Leaf Width (cm) | Lodging (%) | Percent Tertiary | Plant Height (cm) | Seed Pubescence |
|---|---|---|---|---|---|---|---|---|---|---|
| | | | | Trait (Year 1) | | | | | | |
| 100 | 1.3 | 2.9 | 0.0 | 6.0 | 1.9 | 0.9 | 100.0 | 85.0 | 124.3 | 4.0 |
| 96 | 1.0 | 2.7 | 0.0 | 6.0 | 2.2 | 0.7 | 55.6 | 84.4 | 107.4 | 0.0 |
| | | | | Traits (Year 2) | | | | | | |
| 100 | 1.0 | 2.5 | 0.0 | 1.4 | 2.9 | 0.9 | 74.4 | 95.1 | 146.4 | 4.0 |
| 96 | 1.0 | 3.1 | 0.0 | 1.4 | 4.3 | 0.9 | 51.9 | 98.3 | 128.0 | 0.0 |
| 100.2 | 1.0 | 2.4 | 1.0 | 4.6 | 6.8 | 1.0 | 0.0 | 84.6 | 108.4 | 3.5 |
| 96.5 | 1.0 | 3.1 | 1.0 | 3.5 | 8.0 | 0.9 | 0.0 | 81.4 | 84.5 | 0.0 |
| | | | | Trait (Year 3) | | | | | | |
| 100.2.231 | 1.5 | 3.5 | 1.0 | 3.4 | 8.0 | 1.6 | 0.0 | 45.8 | 90.5 | 3.3 |
| 100.2.233 | 1.5 | 2.9 | 0.8 | 3.3 | 5.1 | 1.9 | 0.0 | 78.3 | 105.7 | 3.2 |
| 100.2.235 | 1.0 | 2.8 | 0.8 | 4.9 | 8.0 | 2.1 | 0.0 | 19.3 | 103.5 | 3.7 |
| 96.5.34 | 0.7 | 2.8 | 1.0 | 3.1 | 8.8 | 1.3 | 0.0 | 14.7 | 83.6 | 0.1 |
| 96.5.55 | 1.0 | 3.2 | 1.0 | 3.1 | 8.2 | 1.3 | 0.0 | 17.8 | 83.3 | 0.0 |
| 96.5.6 | 1.0 | 3.3 | 1.0 | 3.3 | 8.6 | 1.4 | 0.0 | 43.8 | 84.8 | 0.1 |
| | | | | Trait (Year 4) | | | | | | |
| 100 | 1.0 | 2.5 | 0.0 | 0.0 | 2.5 | 1.0 | 70.6 | 93.1 | 141.4 | 4.0 |
| 96 | 1.0 | 2.8 | 0.0 | 0.0 | 2.3 | 0.9 | 55.6 | 97.0 | 126.1 | 0.0 |
| 100.2.231 | 1.0 | 2.3 | 1.0 | 3.0 | 2.0 | 1.0 | 0.0 | 80.0 | 86.0 | 3.0 |
| 100.2.233 | 1.0 | 2.4 | 1.0 | 3.0 | 2.0 | 1.8 | 0.0 | 80.0 | 86.0 | 4.0 |
| 100.2.235 | 0.2 | 2.9 | 1.0 | 3.0 | 4.0 | 1.3 | 13.8 | 48.1 | 91.2 | 0.7 |
| 96.5.34 | 0.1 | 2.8 | 1.0 | 3.0 | 4.0 | 1.8 | 0.0 | 17.2 | 86.2 | 0.0 |
| 96.5.55 | 0.3 | 3.0 | 1.0 | 3.0 | 4.0 | 1.8 | 15.0 | 18.3 | 89.0 | 0.0 |
| 96.5.6 | 0.2 | 3.0 | 1.0 | 3.0 | 4.0 | 1.6 | 0.0 | 22.0 | 83.0 | 0.0 |

Table 3 shows improvements in sterility, tiller number, number of seeds, panicles and leaf angle achieved for varieties 96.5.6, 96.5.34, 96.5.55, and 100.2.235, and improvements in sterility, tiller number, number of seeds, and panicles of 100.2.231 and 100.2.233 over lines 100 and 96.

TABLE 3

Traits across tetraploid oat lines

| Line_ID | Leaf Angle | No. of Panicles | No. of Seed | No. of Tillers | Sterility |
|---|---|---|---|---|---|
| 100 | 0.0 | 2.6 | 9.8 | 3.6 | 60.0 |
| 96 | 0.0 | 2.9 | 12.8 | 4.3 | 24.6 |
| 100.2.231 | 0.0 | 3.0 | 20.5 | 5.0 | 9.0 |

TABLE 3-continued

Traits across tetraploid oat lines

| Line_ID | Leaf Angle | No. of Panicles | No. of Seed | No. of Tillers | Sterility |
|---|---|---|---|---|---|
| 100.2.233 | 0.0 | 3.0 | 16.0 | 7.0 | 3.0 |
| 100.2.235 | 1.0 | 4.5 | 22.6 | 6.3 | 1.3 |
| 96.5.34 | 1.0 | 6.1 | 18.9 | 9.6 | 1.0 |
| 96.5.55 | 1.0 | 6.8 | 18.5 | 9.4 | 2.0 |
| 96.5.6 | 1.0 | 4.5 | 17.9 | 6.0 | 3.8 |

Table 4 shows traits across tetraploid oat lines as compared to selected *A. sativa* lines, wild type *A. magna* accessions, wild type *A. murphyii* accessions, and wild type *A. strigosa* accessions.

TABLE 4

| | | | Growth Habit | | |
|---|---|---|---|---|---|
| Line ID | Taxon | Seed Source | Growth Habit (0 = prostrate, 1 = erect) | Maturity (Days from planting until 50% flowering) | Season (1 - very early, 2 - early, 3 - mid-season, 4 - late, 5 - very late, 6 - extremely late) | Plant Height Plant height (cm) |
| 324 | *A. sativa* | GMI Elite | 1.0 | 116.3 | 3.0 | 139.5 |
| 357 | *A. sativa* | GMI Elite | 1.0 | 124.0 | 3.0 | 140.8 |
| 423 | *A. sativa* | GMI Elite | 1.0 | 118.5 | 3.0 | 141.3 |
| Dancer | *A. sativa* | GMI Elite | 1.0 | 127.0 | 3.0 | 141.3 |
| Leggett | *A. sativa* | GMI Elite | 1.0 | 120.3 | 3.0 | 146.0 |
| Morgan | *A. sativa* | GMI Elite | 1.0 | 163.0 | 3.5 | 133.0 |
| Triactor | *A. sativa* | GMI Elite | 0.0 | 125.3 | 3.0 | 136.5 |
| 100 | *A. magna* | This application | 0.0 | 141.5 | 4.0 | 175.2 |

TABLE 4-continued

| Line ID | Species | Source | | | | |
|---|---|---|---|---|---|---|
| 100.2.235 | A. magna | This application | 1.0 | 118.8 | 1.0 | 125.5 |
| 96 | A. magna | This application | 0.0 | 135.5 | 4.0 | 189.5 |
| 96.5.34 | A. magna | This application | 1.0 | 123.0 | 1.0 | 135.5 |
| 96.5.55 | A. magna | This application | 1.0 | 112.8 | 1.0 | 143.3 |
| 96.5.6 | A. magna | This application | 1.0 | 116.8 | 3.0 | 142.5 |
| PI657620 | A. magna | NSGC | 0.0 | 124.0 | 4.0 | 183.2 |
| Clav8330 | A. magna | NSGC | 0.0 | 120.3 | 3.5 | 157.8 |
| PI659392 | A. magna | NSGC | 0.0 | 148.0 | 4.0 | 166.5 |
| PI659401 | A. magna | NSGC | 0.0 | 141.8 | 1.0 | 150.8 |
| Clav7010 | A. strigosa | NSGC | 0.0 | 114.5 | 2.0 | 179.8 |
| PI401794 | A. strigosa | NSGC | 0.0 | 121.3 | 1.0 | 164.0 |
| PI436103 | A. strigosa | NSGC | 1.0 | 116.5 | 1.0 | 176.8 |
| PI657356 | A. murphyi | NSGC | 0.0 | 163.0 | 5.0 | 152.3 |
| PI657361 | A. murphyi | NSGC | 0.0 | 163.0 | 5.0 | 207.0 |
| PI657380 | A. murphyi | NSGC | 0.0 | 163.0 | 5.0 | 207.8 |
| PI657606 | A. murphyi | NSGC | 0.0 | 163.0 | 5.0 | 193.0 |

| | Stem | | | | |
|---|---|---|---|---|---|
| Line ID | Diameter (mm) | Upper Culm Hairiness (1 - Hairless, 2 - Hairy) | Mature Stem Color (1 - Yellow, 2 - Reddish) | No. of tillers (count) | Lodging (%) |
| 324 | 6.5 | 1.0 | 1.0 | 17.8 | 0.0 |
| 357 | 5.3 | 1.0 | 1.0 | 12.5 | 10.0 |
| 423 | 5.5 | 1.0 | 1.0 | 12.0 | 0.0 |
| Dancer | 6.5 | 1.0 | 1.0 | 15.0 | 5.0 |
| Leggett | 7.0 | 1.0 | A. s12.5 | 12.5 | 15.0 |
| Morgan | 7.0 | 1.0 | 1.0 | 7.5 | 7.5 |
| Triactor | 6.0 | 1.0 | 1.0 | 13.8 | 5.0 |
| 100 | 5.8 | 2.0 | 2.0 | 15.5 | 70.0 |
| 100.2.235 | 4.0 | 1.0 | 2.0 | 22.5 | 6.3 |
| 96 | 6.5 | 1.0 | 2.0 | 11.3 | 51.3 |
| 96.5.34 | 5.3 | 1.0 | 2.0 | 23.7 | 1.7 |
| 96.5.55 | 6.3 | 1.0 | 2.0 | 20.3 | 3.8 |
| 96.5.6 | 5.8 | 1.3 | 2.0 | 21.5 | 5.0 |
| PI657620 | 4.5 | 2.0 | 2.0 | 18.0 | 100.0 |
| Clav8330 | 3.8 | 2.0 | 2.0 | 19.8 | 96.3 |
| PI659392 | 4.0 | 2.0 | 2.0 | 18.8 | 100.0 |
| PI659401 | 4.3 | 2.0 | 2.0 | 20.3 | 100.0 |
| Clav7010 | 5.0 | 1.0 | 1.0 | 11.8 | 93.8 |
| PI401794 | 4.0 | 1.0 | 1.0 | 28.8 | 10.0 |
| PI436103 | 4.5 | 1.0 | 2.0 | 14.0 | 10.0 |
| PI657356 | 4.5 | 1.0 | 2.0 | 12.0 | 43.8 |
| PI657361 | 5.5 | 1.0 | 2.0 | 11.3 | 40.0 |
| PI657380 | 5.8 | 1.0 | 2.0 | 15.8 | 100.0 |
| PI657606 | 6.0 | 1.0 | 2.0 | 9.5 | 92.5 |

| | Leaf | | | | |
|---|---|---|---|---|---|
| Line ID | Carriage/Leaf Angle (1 - Drooping, 2 - Erect) | Color (1 - Yellow/Green, 2 - Light Green, 3 - Dark Green, 4 - Blue/Green) | Penultimate Width (mm) | Ligule (1 - Absent, 2 - Present) | Leaf Margin (1 - Glabrous/Hairless, 2 - Ciliate/Hairy) |
| 324 | 1.0 | 3.0 | 16.8 | 2.0 | 1.0 |
| 357 | 1.0 | 2.0 | 16.5 | 2.5 | 1.0 |
| 423 | 1.0 | 2.3 | 16.8 | 2.0 | 1.0 |
| Dancer | 1.0 | 3.0 | 16.8 | 2.0 | 1.0 |
| Leggett | 1.0 | 2.3 | 16.3 | 2.0 | 1.0 |
| Morgan | 1.0 | 2.5 | 13.3 | 2.0 | 1.0 |
| Triactor | 1.0 | 2.0 | 17.0 | 1.0 | 1.0 |
| 100 | 1.0 | 3.0 | 18.8 | 2.0 | 2.0 |
| 100.2.235 | 2.0 | 2.0 | 13.0 | 2.0 | 1.5 |
| 96 | 1.8 | 2.5 | 16.5 | 1.3 | 2.0 |
| 96.5.34 | 2.0 | 3.0 | 17.7 | 1.0 | 1.0 |
| 96.5.55 | 2.0 | 2.0 | 15.0 | 1.0 | 1.8 |
| 96.5.6 | 2.0 | 3.0 | 14.8 | 2.0 | 2.0 |
| PI657620 | 2.0 | 2.0 | 14.5 | 2.0 | 2.0 |
| Clav8330 | 1.5 | 2.8 | 13.5 | 2.0 | 1.5 |
| PI659392 | 1.0 | 2.5 | 12.0 | 2.0 | 1.5 |
| PI659401 | 1.0 | 2.0 | 16.3 | 2.0 | 1.5 |
| Clav7010 | 2.0 | 3.0 | 13.5 | 1.3 | 1.0 |
| PI401794 | 1.0 | 2.0 | 11.0 | 1.0 | 1.0 |
| PI436103 | 1.0 | 2.5 | 13.3 | 1.0 | 1.0 |
| PI657356 | 1.0 | 2.5 | 16.5 | 1.5 | 2.0 |

TABLE 4-continued

| | | | | | |
|---|---|---|---|---|---|
| PI657361 | 1.0 | 3.0 | 15.3 | 1.0 | 2.0 |
| PI657380 | 2.0 | 2.0 | 16.5 | 2.0 | 2.0 |
| PI657606 | 2.0 | 2.0 | 16.8 | 2.0 | 2.0 |

| | Leaf | | | | |
|---|---|---|---|---|---|
| Line ID | Leaf Sheath (1 - Hairless, 2 - Hairy) | Leaf density (0 = thin, 1 = medium, 2 = dense) | Heading date (days from planting) | Panicle Shape (1- Equilateral, 2 - Intermediate, 3 - Unilateral) | Attachment of Lower Whorl of Branches (1 - First Node, 2 - Second Node/False Node) |
| 324 | 1.0 | 2.0 | 50.0 | 1.5 | 1.0 |
| 357 | 1.0 | 1.0 | 50.0 | 1.0 | 1.0 |
| 423 | 1.0 | 1.0 | 50.0 | 1.0 | 1.0 |
| Dancer | 1.0 | 2.0 | 50.0 | 1.0 | 1.0 |
| Leggett | 1.0 | 1.8 | 57.0 | 1.0 | 1.0 |
| Morgan | 1.0 | 0.5 | 74.0 | 2.0 | 1.0 |
| Triactor | 1.0 | 1.3 | 61.0 | 1.0 | 1.0 |
| 100 | 1.0 | 2.0 | 75.0 | 1.3 | 1.0 |
| 100.2.235 | 1.0 | 1.0 | 50.0 | 1.0 | 1.0 |
| 96 | 2.0 | 0.5 | 75.0 | 1.5 | 1.0 |
| 96.5.34 | 1.0 | 2.0 | 57.0 | 1.7 | 1.0 |
| 96.5.55 | 1.0 | 2.0 | 50.0 | 1.8 | 1.0 |
| 96.5.6 | 1.0 | 2.0 | 53.5 | 2.0 | 1.0 |
| PI657620 | 1.0 | 2.0 | 109.0 | 1.0 | 1.0 |
| Clav8330 | 1.0 | 1.0 | 90.5 | 2.0 | 1.0 |
| PI659392 | 1.0 | 1.0 | 106.0 | 2.0 | 1.0 |
| PI659401 | 1.0 | 1.0 | 72.0 | 2.0 | 1.0 |
| Clav7010 | 1.0 | 0.0 | 66.0 | 1.3 | 2.0 |
| PI401794 | 1.0 | 2.0 | 60.0 | 2.0 | 1.0 |
| PI436103 | 1.0 | 1.5 | 62.0 | 1.0 | 1.0 |
| PI657356 | 1.0 | 1.0 | 88.3 | 2.0 | 1.0 |
| PI657361 | 1.0 | 2.0 | 107.0 | 3.0 | 1.0 |
| PI657380 | 1.0 | 1.5 | 98.5 | 1.0 | 1.0 |
| PI657606 | 1.0 | 1.0 | 106.0 | 3.0 | 2.0 |

| Line ID | No. of panicles (count) | Panicle Width (cm) | Panicle Length (cm) | Number of Branches (count) | Position of Branches (1 - Ascending, 2 - Spreading, 3 - Drooping, 4 - Pectinate, 5 - Confused) |
|---|---|---|---|---|---|
| 324 | 8.0 | 92.5 | 178.8 | 4.8 | 2.0 |
| 357 | 5.8 | 132.5 | 220.0 | 4.5 | 3.0 |
| 423 | 7.8 | 116.3 | 197.5 | 4.8 | 2.0 |
| Dancer | 7.3 | 107.5 | 190.0 | 5.8 | 1.5 |
| Leggett | 4.8 | 97.5 | 175.0 | 5.0 | 2.5 |
| Morgan | 3.3 | 77.5 | 234.5 | 5.5 | 1.0 |
| Triactor | 8.5 | 80.0 | 307.5 | 5.8 | 1.0 |
| 100 | 8.3 | 120.0 | 210.0 | 5.5 | 3.0 |
| 100.2.235 | 10.3 | 125.0 | 167.5 | 4.0 | 2.5 |
| 96 | 6.8 | 192.5 | 255.0 | 4.0 | 3.0 |
| 96.5.34 | 11.7 | 120.0 | 186.7 | 4.3 | 1.0 |
| 96.5.55 | 14.0 | 280.8 | 203.8 | 5.0 | 1.0 |
| 96.5.6 | 11.3 | 102.5 | 180.0 | 4.5 | 2.0 |
| PI657620 | 8.5 | 130.0 | 155.0 | 5.0 | 3.0 |
| Clav8330 | 10.5 | 96.3 | 203.8 | 4.3 | 3.0 |
| PI659392 | 8.0 | 101.3 | 200.0 | 3.8 | 3.0 |
| PI659401 | 9.0 | 118.8 | 225.0 | 4.0 | 3.0 |
| Clav7010 | 10.0 | 123.8 | 227.5 | 6.3 | 1.0 |
| PI401794 | 20.3 | 107.5 | 201.3 | 6.3 | 2.0 |
| PI436103 | 11.3 | 117.5 | 222.5 | 6.3 | 2.0 |
| PI657356 | 5.8 | 125.0 | 227.5 | 5.5 | 1.5 |
| PI657361 | 6.0 | 128.8 | 248.8 | 6.0 | 1.0 |
| PI657380 | 7.8 | 147.5 | 182.5 | 4.8 | 2.0 |
| PI657606 | 5.5 | 103.8 | 220.0 | 5.3 | 2.5 |

| | | | Rachis | | |
|---|---|---|---|---|---|
| Line ID | No. seed per panicle (count) | Shape (1 - Recurved, 2 - Erect/Straight) | Second Floret Segment Length (mm) | Second Floret Segment Pubescence (1 - Hairless, 2 - Hairy) | Rachilla Hairs (1 - Short, 2 - Long) |
| 324 | 20.5 | 1.0 | 51.3 | 1.0 | 2.0 |
| 357 | 26.5 | 1.0 | 56.3 | 1.0 | 2.0 |
| 423 | 31.5 | 1.0 | 53.3 | 1.0 | 2.0 |
| Dancer | 40.3 | 1.5 | 58.8 | 1.0 | 2.0 |
| Leggett | 24.8 | 1.0 | 49.0 | 1.0 | 2.0 |
| Morgan | 35.8 | 1.0 | 58.8 | 1.0 | 2.0 |
| Triactor | 19.8 | 2.0 | 48.8 | 1.0 | 2.0 |

TABLE 4-continued

| Line ID | | | | | |
|---|---|---|---|---|---|
| 100 | 23.8 | 1.0 | 49.5 | 1.0 | 2.0 |
| 100.2.235 | 18.0 | 1.5 | 43.0 | 1.0 | 2.0 |
| 96 | 19.8 | 1.0 | 77.5 | 1.0 | 2.0 |
| 96.5.34 | 20.0 | 1.0 | 51.7 | 1.0 | 2.0 |
| 96.5.55 | 24.3 | 1.0 | 53.5 | 1.0 | 2.0 |
| 96.5.6 | 19.5 | 1.0 | 46.3 | 1.0 | 2.0 |
| PI657620 | 24.0 | 1.0 | 62.5 | 1.0 | 2.0 |
| Clav8330 | 11.5 | 1.0 | 60.0 | 1.0 | 2.0 |
| PI659392 | 10.8 | 2.0 | 68.8 | 1.0 | 2.0 |
| PI659401 | 12.8 | 2.0 | 63.8 | 1.0 | 2.0 |
| Clav7010 | 89.8 | 1.5 | 56.8 | 1.0 | 2.0 |
| PI401794 | 63.3 | 1.0 | 40.0 | 1.0 | 2.0 |
| PI436103 | 79.5 | 2.0 | 50.0 | 1.0 | 2.0 |
| PI657356 | 22.3 | 1.0 | 51.3 | 1.0 | 2.0 |
| PI657361 | 18.0 | 1.0 | 46.0 | 1.0 | 2.0 |
| PI657380 | 20.3 | 1.0 | 43.8 | 1.0 | 2.0 |
| PI657606 | 19.5 | 1.0 | 48.8 | 1.0 | 2.0 |

| | Spikelet | | | | |
|---|---|---|---|---|---|
| Line ID | Spikelet Separation (1 - Abscission, 2 - Semi-Abscission, 3 - Fracture) | Floret Separation (1 - Disarticulation, 2 - Heterofracture, 3 - Basifracture) | Shattering (1 - None, 2 - Minimal, 3 - Medium, 4 - Severe | Basal Hair (1 - Hairless, 2 - Hairy) | Basal Hair Color (0 - Absent, 1 - White, 2 - Yellow, 3 - Red, 4 - Gray, 5 - Black) |
| 324 | 1.0 | 1.0 | 1.0 | 1.0 | 0.0 |
| 357 | 1.0 | 1.0 | 1.0 | 1.0 | 0.0 |
| 423 | 1.0 | 1.0 | 1.0 | 1.0 | 0.0 |
| Dancer | 1.0 | 1.0 | 1.0 | 1.0 | 0.0 |
| Leggett | 1.0 | 1.0 | 1.0 | 1.0 | 0.0 |
| Morgan | 1.0 | 1.0 | 1.0 | 1.0 | 0.0 |
| Triactor | 1.0 | 1.0 | 1.0 | 1.0 | 0.0 |
| 100 | 3.0 | 3.0 | 4.0 | 2.0 | 2.0 |
| 100.2.235 | 1.0 | 1.0 | 1.3 | 1.0 | 0.0 |
| 96 | 3.0 | 3.0 | 3.3 | 2.0 | 4.0 |
| 96.5.34 | 1.0 | 1.0 | 1.0 | 1.0 | 0.0 |
| 96.5.55 | 1.0 | 1.0 | 1.0 | 1.0 | 0.0 |
| 96.5.6 | 1.0 | 1.0 | 1.0 | 1.0 | 0.0 |
| PI657620 | 3.0 | 3.0 | 4.0 | 2.0 | 3.0 |
| Clav8330 | 3.0 | 3.0 | 4.0 | 2.0 | 2/3 |
| PI659392 | 3.0 | 3.0 | 4.0 | 2.0 | 3/5 |
| PI659401 | 3.0 | 3.0 | 4.0 | 2.0 | 2/3 |
| Clav7010 | 1.0 | 1.0 | 1.0 | 1.0 | 0.0 |
| PI401794 | 1.0 | 1.0 | 1.0 | 1.0 | 0.0 |
| PI436103 | 1.0 | 1.0 | 1.0 | 1.0 | 0.0 |
| PI657356 | 3.0 | 3.0 | 4.0 | 2.0 | 2/3 |
| PI657361 | 3.0 | 3.0 | 4.0 | 2.0 | 2.0 |
| PI657380 | 3.0 | 3.0 | 4.0 | 2.0 | 2.0 |
| PI657606 | 3.0 | 3.0 | 4.0 | 2.0 | 2.0 |

| | Spikelet | | Glumes | | |
|---|---|---|---|---|---|
| Line ID | Florets per Spikelet (count) | Sterile Spikelets (% - no. out of 10) | Width (mm) | Length (mm) | Number of Veins (count) |
| 324 | 2.0 | 2.5 | 5.8 | 20.0 | 9.3 |
| 357 | 2.8 | 2.5 | 6.0 | 24.8 | 10.3 |
| 423 | 2.0 | 2.5 | 5.8 | 22.3 | 9.0 |
| Dancer | 2.3 | 17.5 | 5.8 | 21.8 | 9.5 |
| Leggett | 2.0 | 7.5 | 5.0 | 22.3 | 10.5 |
| Morgan | 2.0 | 5.0 | 6.5 | 22.5 | 9.8 |
| Triactor | 2.0 | 5.0 | 5.3 | 19.8 | 10.0 |
| 100 | 2.0 | 17.5 | 8.8 | 35.3 | 10.5 |
| 100.2.235 | 2.0 | 2.5 | 6.3 | 32.8 | 9.3 |
| 96 | 3.0 | 30.0 | 8.0 | 39.3 | 9.8 |
| 96.5.34 | 2.3 | 13.3 | 7.0 | 32.3 | 9.3 |
| 96.5.55 | 2.5 | 2.5 | 7.0 | 31.3 | 9.3 |
| 96.5.6 | 2.8 | 27.5 | 5.0 | 33.5 | 8.0 |
| PI657620 | 3.0 | 0.0 | 7.5 | 41.0 | 8.5 |
| Clav8330 | 3.8 | 22.5 | 8.0 | 37.0 | 10.0 |
| PI659392 | 3.0 | 2.5 | 8.3 | 44.5 | 10.8 |
| PI659401 | 3.0 | 25.0 | 7.3 | 37.5 | 9.8 |

TABLE 4-continued

| Line ID | Glumes Color (1 - White, 2 - Yellow, 3 - Red, 4 - Striped) | Length (mm) | Lemma Color (1 - White, 2 - Yellow, 3 - Red, 4 - Gray, 5 - Black) | Hairiness of Dorsal Surface (1 - Hairless, 2 - Hairy) | Awn (First Floret) Occurrence (1 - Absent, 2 - Infrequent, 3 - Common, 4 - Frequent) |
|---|---|---|---|---|---|
| Clav7010 | 1.0 | 5.0 | 4.0 | 19.0 | 8.0 |
| PI401794 | 3.0 | 0.0 | 2.5 | 23.3 | 7.0 |
| PI436103 | 1.0 | 0.0 | 4.5 | 17.8 | 7.8 |
| PI657356 | 3.0 | 30.0 | 10.3 | 43.3 | 9.3 |
| PI657361 | 3.0 | 67.5 | 10.8 | 46.0 | 8.5 |
| PI657380 | 3.0 | 2.5 | 8.3 | 42.0 | 10.8 |
| PI657606 | 3.5 | 75.0 | 8.0 | 43.8 | 7.5 |

| Line ID | Glumes Color (1 - White, 2 - Yellow, 3 - Red, 4 - Striped) | Length (mm) | Lemma Color (1 - White, 2 - Yellow, 3 - Red, 4 - Gray, 5 - Black) | Hairiness of Dorsal Surface (1 - Hairless, 2 - Hairy) | Awn (First Floret) Occurrence (1 - Absent, 2 - Infrequent, 3 - Common, 4 - Frequent) |
|---|---|---|---|---|---|
| 324 | 4.0 | 14.5 | 2.0 | 1.0 | 2.8 |
| 357 | 2.0 | 17.0 | 2.0 | 1.0 | 1.0 |
| 423 | 1.0 | 16.3 | 2.0 | 1.0 | 2.3 |
| Dancer | 1.0 | 14.8 | 2.0 | 1.0 | 1.0 |
| Leggett | 1.0 | 15.0 | 1.8 | 1.0 | 1.0 |
| Morgan | 1.0 | 13.5 | 1.0 | 1.0 | 1.0 |
| Triactor | 1.0 | 14.0 | 2.0 | 1.0 | 1.0 |
| 100 | 1.0 | 24.0 | 2.0 | 1.0 | 4.0 |
| 100.2.235 | 4.0 | 19.0 | 2.0 | 2.0 | 2.5 |
| 96 | 1.0 | 28.3 | 4.0 | 1.0 | 4.0 |
| 96.5.34 | 1.0 | 23.3 | 2.0 | 1.0 | 1.0 |
| 96.5.55 | 1.0 | 22.3 | 2.0 | 1.0 | 3.0 |
| 96.5.6 | 1.0 | 22.8 | 2.0 | 1.0 | 2.5 |
| PI657620 | 1.0 | 28.0 | 2/5 | 2.0 | 4.0 |
| Clav8330 | 1.0 | 26.8 | 3/5 | 2.0 | 4.0 |
| PI659392 | 1.0 | 30.5 | 3.0 | 2.0 | 4.0 |
| PI659401 | 1.0 | 28.0 | 2/5 | 2.0 | 4.0 |
| Clav7010 | 1.0 | 15.5 | 2/5 | 1.0 | 3.8 |
| PI401794 | 1.0 | 19.0 | 1/3 | 1.0 | 4.0 |
| PI436103 | 1/3 | 13.8 | 5.0 | 1.0 | 4.0 |
| PI657356 | 1.0 | 28.3 | 3.0 | 1.8 | 4.0 |
| PI657361 | 1.0 | 27.8 | 3.3 | 2.0 | 4.0 |
| PI657380 | 1.0 | 29.5 | 2.0 | 2.0 | 4.0 |
| PI657606 | 1.0 | 26.3 | 2.0 | 1.0 | 4.0 |

| Line ID | Awn (First Floret) Type (0 - Absent, 1 - Non-twisted, 2 - Twisted, 3 - Twisted Geniculate) | Length (mm) | Seed Basal Hair (1 - Absent, 2 - Absent to Few, 3 - Few to Several, 4 - Several to Numerous, 5 - Numerous) | Basal Hair Length (mm) | Individual Groat Weight (mg) |
|---|---|---|---|---|---|
| 324 | 2.0 | 21.0 | 1.0 | 0.0 | 29.2 |
| 357 | 1.0 | 0.0 | 1.0 | 0.0 | 46.5 |
| 423 | 1.0 | 16.5 | 1.0 | 0.0 | 37.9 |
| Dancer | 0.0 | 0.0 | 1.0 | 0.0 | 39.3 |
| Leggett | 0.0 | 0.0 | 1.0 | 0.0 | 38.2 |
| Morgan | 0.0 | 0.0 | 1.0 | 0.0 | 35.6 |
| Triactor | 0.0 | 0.0 | 1.0 | 0.0 | 31.3 |
| 100 | 3.0 | 47.8 | 5.0 | 5.3 | 48.4 |
| 100.2.235 | 2.0 | 30.8 | 1.0 | 0.0 | 35.0 |
| 96 | 3.0 | 64.5 | 5.0 | 7.5 | 51.3 |
| 96.5.34 | 0.0 | 0.0 | 1.0 | 0.0 | 37.5 |
| 96.5.55 | 2.0 | 35.5 | 3.0 | 4.8 | 46.7 |
| 96.5.6 | 2.0 | 34.3 | 2.0 | 3.8 | 35.0 |
| PI657620 | 3.0 | 66.5 | 5.0 | 7.5 | 45.7 |
| Clav8330 | 3.0 | 58.5 | 5.0 | 10.5 | 45.8 |
| PI659392 | 3.0 | 65.3 | 5.0 | 6.3 | 38.9 |
| PI659401 | 3.0 | 61.3 | 5.0 | 6.5 | 30.5 |
| Clav7010 | 2.0 | 13.5 | 1.0 | 0.0 | 21.0 |
| PI401794 | 1.0 | 23.5 | 1.0 | 0.0 | 8.8 |
| PI436103 | 3.0 | 20.3 | 1.0 | 0.0 | 19.3 |
| PI657356 | 3.0 | 70.5 | 5.0 | 5.0 | 11.4 |
| PI657361 | 3.0 | 70.8 | 5.0 | 8.5 | 12.6 |
| PI657380 | 3.0 | 68.3 | 5.0 | 5.0 | 28.0 |
| PI657606 | 3.0 | 72.5 | 5.0 | 10.5 | 8.9 |

TABLE 4-continued

| Line ID | Groat length (mm) | Groat width (mm) | Groat color (0 = light tan, 1 = brown, 2 = dark brown) | Groat pubescence (0 = none, 1 = minimal, 2 = medium, 3 = dense) | Ease of dehulling (0 = easy, 1 = medium, 2 = hard) |
|---|---|---|---|---|---|
| 324 | 9.3 | 3.5 | 1.0 | 1.0 | 0.0 |
| 357 | 10.8 | 3.0 | 1.0 | 2.0 | 0.0 |
| 423 | 11.0 | 3.3 | 1.0 | 1.8 | 0.0 |
| Dancer | 10.5 | 3.8 | 1.0 | 1.0 | 030 |
| Leggett | 10.8 | 3.3 | 1.0 | 1.0 | 030 |
| Morgan | 11.0 | 3.0 | 0.0 | 1.0 | 030 |
| Triactor | 10.5 | 3.0 | 0.0 | 1.0 | 030 |
| 100 | 12.3 | 4.0 | 1.0 | 2.0 | 2.0 |
| 100.2.235 | 10.8 | 3.0 | 1.0 | 1.0 | 0.0 |
| 96 | 12.0 | 4.0 | 1.0 | 2.0 | 2.0 |
| 96.5.34 | 11.3 | 4.0 | 1.0 | 1.0 | 1.0 |
| 96.5.55 | 12.5 | 4.0 | 1.0 | 1.0 | 0.0 |
| 96.5.6 | 11.8 | 3.8 | 1.0 | 1.0 | 1.0 |
| PI657620 | 14.5 | 4.0 | 5.0 | 3.0 | 2.0 |
| Clav8330 | 10.5 | 4.3 | 2.0 | 3.0 | 2.0 |
| PI659392 | 11.8 | 3.8 | 1.0 | 3.0 | 2.0 |
| PI659401 | 11.8 | 4.0 | 0.0 | 3.0 | 2.0 |
| Clav7010 | 10.0 | 2.0 | 0.0 | 1.0 | 2.0 |
| PI401794 | 7.5 | 2.0 | 0.0 | 1.0 | 0.0 |
| PI436103 | 9.8 | 2.0 | 1.0 | 1.0 | 0.0 |
| PI657356 | 10.5 | 4.0 | 0.0 | 3.0 | 2.0 |
| PI657361 | 10.0 | 4.0 | 0.0 | 3.0 | 2.0 |
| PI657380 | 11.3 | 4.0 | 0.0 | 3.0 | 2.0 |
| PI657606 | 10.3 | 4.0 | 0.0 | 3.0 | 2.0 |

Example 2—Tetraploid Oat Line Nutritional Traits

Nutrition

FIG. 2 is a graph showing the grain content of fats, amino acids, fatty acids as measured in whole grain flour of *A. magna* ssp *domestica* line 100.2 and 96.5 compared to Leggett. As can be seen the varieties of the invention are higher in zinc, protein, amino acid, unsaturated and polyunsaturated fatty acids.

Figure 3:
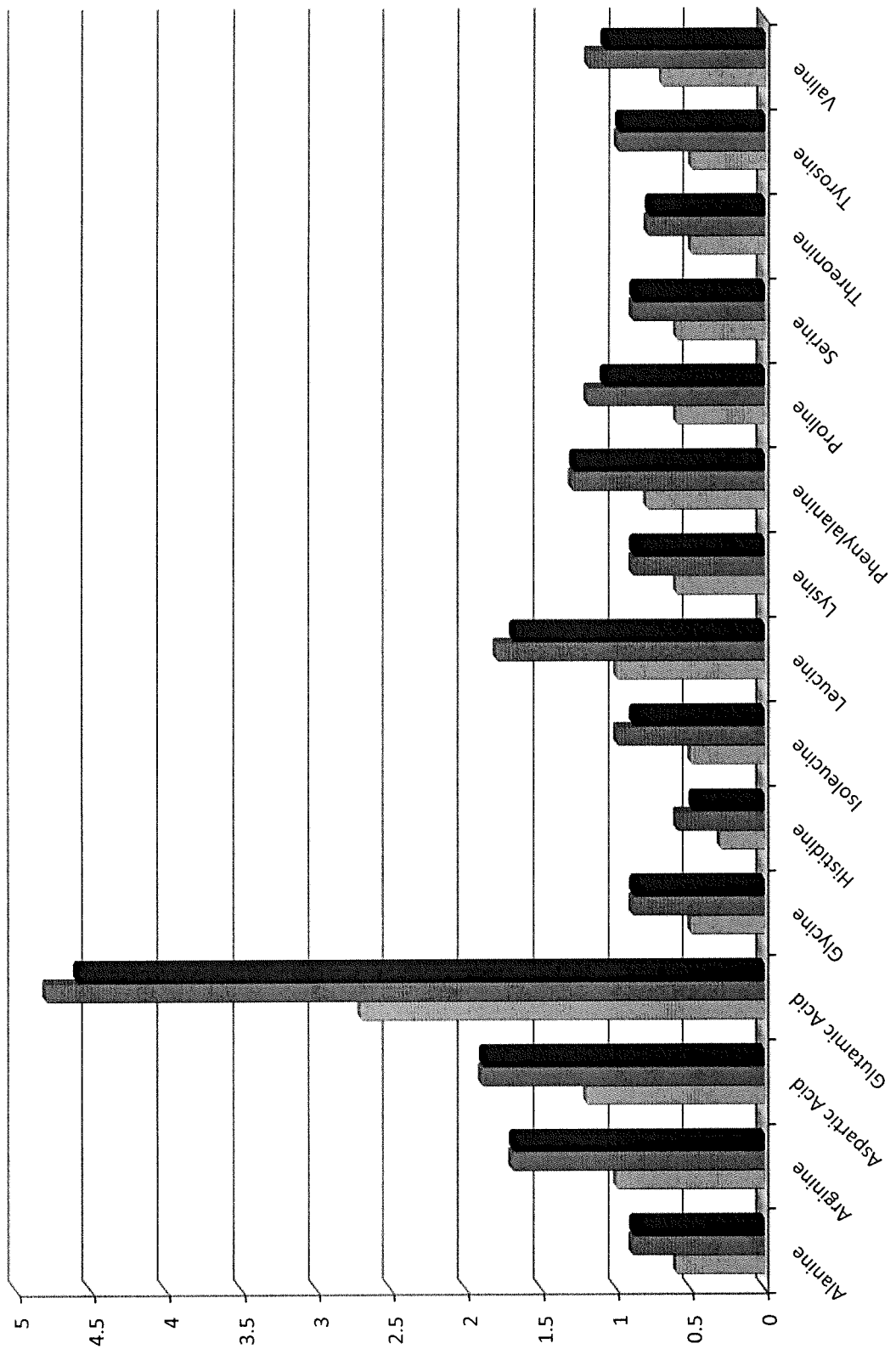
FIG. 3 is a graph showing the percent of free essential amino acids as measured in whole grain flour. *A. sativa* 'Leggett' was used as the hexaploid oat control to compare with two examples of tetraploid oat lines of the invention. All analytical measurements were performed at Medallion Lab in Minneapolis, Minn. *A. sativa* 'Leggett' is a hexaploid *Avena sativa* hulled spring oat variety that is a standard check for oats. Spring oat varieties typically take 82-98 days from seedling to maturity.

FIG. 3 is a graph showing the amino acid content and distribution of line 100.2 and line 96.5 compared to Leggett as measured in whole grain flour. The graph demonstrates that the varieties of the invention are much higher in arginine, glutamic and aspartic acids compared to Leggett, and are in fact, higher in every amino acid.

Figure 4:
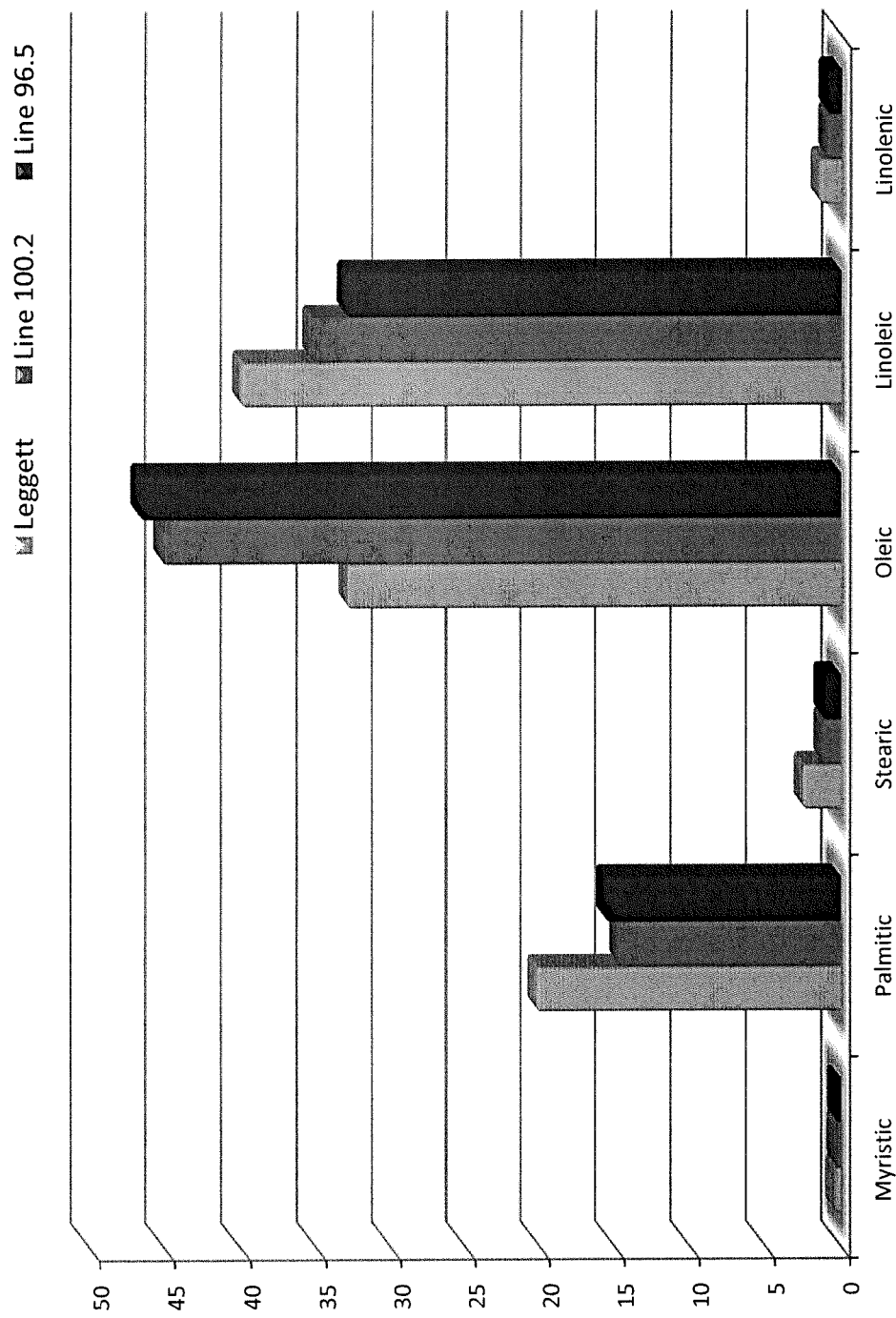
FIG. 4 is a graph showing the percent of fatty acids as measured in whole grain flour. *A. sativa* 'Leggett' was used as the hexaploid oat control to compare with two tetraploid oat lines. The tetraploid oat lines exhibit an increased oleic content over *A. sativa* 'Leggett' and decreased linoleic content over *A. sativa* 'Leggett'. All analytical measurements were performed at Medallion Lab in Minneapolis, Minn.

FIG. 4 is a graph showing the fatty acid content and distribution of line 100.2 and line 96.5 compared to Leggett as measured in whole grain flour. The graph shows that the varieties of the invention are much higher in oleic acid, linoleic, linolenic and palmitic, the unsaturated fatty acids that stearic and myristic where they are lower than Leggett.

Additional nutritional trait comparisons were made with some *A. magna* ssp *domestica* lines (96.5.34, 100.2.235, and 96.5.6) with a hexaploid control. Results are shown in Tables 5-11.

From Table 5, one can see that the tetraploid oat lines have more than double the protein content of control hexaploid lines.

TABLE 5

General nutritional composition

| Sample | Calories (100 g) | Carbohydrates (%) | Total Cholesterol mg/100 mg | Starch (%) | Ash (%) | Protein (%) |
|---|---|---|---|---|---|---|
| Hexaploid control | 379 | 67.3 | | 56.2 | 1.848 | 12.90 |
| Hexaploid control | 374 | 66.3 | <1.0 | 57.1 | 1.802 | 12.80 |
| Tetraploid line 96.5.34 | 397 | 55.4 | <1.0 | 49.6 | 2.380 | 26.50 |
| Tetraploid line 100.2.235 | 399 | 53.5 | <1.0 | | 2.188 | 26.00 |
| Tetraploid line 96.5.6 | 393 | 53.5 | 1.16 | | 2.379 | 25.90 |

From Table 6 one can see that *A. magna* ssp *domestica* lines can have a lower beta glucan content than traditional hexaploid oat varieties.

TABLE 6

Fiber and beta glucan content

| Sample | β-Glucan (%) | Insoluble Fiber (%) | Soluble Fiber (%) | Total Fiber (%) |
|---|---|---|---|---|
| Hexaploid control | 4.48 | 5.7 | 6.5 | 12.2 |
| Hexaploid control | 4.19 | 5.8 | 5.8 | 11.6 |

TABLE 6-continued

Fiber and beta glucan content

| Sample | β-Glucan (%) | Insoluble Fiber (%) | Soluble Fiber (%) | Total Fiber (%) |
|---|---|---|---|---|
| Tetraploid line 96.5.34 | 2.53 | 3.4 | 4.8 | 8.2 |
| Tetraploid line 100.2.235 | 3.05 | 3.8 | 5.1 | 8.9 |
| Tetraploid line 96.5.62014 | 2.25 | 3.6 | 5.1 | 8.7 |

From Table 7 one can see that *A. magna* ssp *domestica* lines can have higher total fatty acid percentage and a lower saturated acid percentage than traditional hexaploid oat varieties.

TABLE 7

Fatty acid content profile

| Sample | Total Fat (%) | Sat Fat (%) | Mono Sat Fat (%) | cis-cis Poly Fat (%) | Trans Fat (%) |
|---|---|---|---|---|---|
| Hexaploid control | 6.47 | 1.24 | 2.37 | 2.57 | 0.00 |
| Hexaploid control | 6.38 | 1.24 | 2.34 | 2.51 | 0.00 |
| Tetraploid line 96.5.34 | 7.70 | 1.44 | 3.25 | 2.67 | 0.01 |
| Tetraploid line 100.2.235 | 9.04 | 1.64 | 4.01 | 2.99 | 0.01 |
| Tetraploid line 96.5.6 | 8.33 | 1.52 | 3.60 | 2.83 | 0.01 |

From Tables 8 and 9, one can see that *A. magna* ssp *domestica* lines can have a higher oleic acid content and lower content of saturated fatty acids than traditional hexaploid oat varieties.

TABLE 8

Fatty acid content profile

| Sample | 10:0 Capric | 12:0 Lauric | 14:0 Myristic | 16:0 Palmitic | 16:1 Palmitoleic | 18:0 Stearic | 18:1 Oleic |
|---|---|---|---|---|---|---|---|
| Hexaploid control | | 0.031 | 0.278 | 17.929 | 0.115 | 1.561 | 37.172 |
| Hexaploid control | | | 0.267 | 18.115 | 0.173 | 1.600 | 37.061 |
| Tetraploid line 96.5.34 | | 0.052 | 0.428 | 17.420 | 0.143 | 1.233 | 42.757 |
| Tetraploid line 100.2.235 | | 0.033 | 0.387 | 17.072 | 0.144 | 1.084 | 45.143 |
| Tetraploid line 96.5.6 | 0.012 | 0.048 | 0.384 | 17.021 | 0.144 | 1.273 | 44.012 |

TABLE 9

Fatty acid content profile

| Sample | 18:2 Linoleic | 20:0 Arachidic | 20:1 Gadoleci | 18:3 Linolenic | 22:0 Behenic | 24:0 Lignoceric | 24:1 Nervonic |
|---|---|---|---|---|---|---|---|
| Hexaploid control | 40.17 | 0.139 | 0.804 | 1.314 | 0.077 | 0.108 | 0.046 |
| Hexaploid control | 39.853 | 0.157 | 0.863 | 1.286 | 0.078 | 0.157 | 0.125 |
| Tetraploid line 96.5.34 | 35.397 | 0.130 | 0.883 | 0.844 | 0.078 | 0.195 | 0.104 |
| Tetraploid line 100.2.235 | 33.603 | 0.111 | 0.907 | 0.885 | 0.066 | 0.177 | 0.089 |
| Tetraploid line 96.5.6 | 34.619 | 0.120 | 0.901 | 0.877 | 0.072 | 0.192 | 0.084 |

From Table 10 one can see that *A. magna* ssp *domestica* lines can have a higher iron, magnesium, and/or zinc content than traditional hexaploid oat varieties.

TABLE 10

Mineral profile

| Sample | Calcium (mg/100 g) | Iron (mg/100 g) | Magnesium (mg/100 g) | Zinc (mg/100 g) |
|---|---|---|---|---|
| Hexaploid control | 52.10 | 4.03 | 139.00 | 2.42 |
| Tetraploid line 96.5.6 | 49.90 | 7.75 | —* | 5.52 |
| Tetraploid line 96.5.34 | 54.30 | 10.50 | 186.00 | 6.15 |
| Tetraploid line 100.2.235 | 47.50 | 9.13 | 183.00 | 6.69 |

*not measured

From Table 11 one can see that *A. magna* ssp *domestica* lines can have a higher vitamin B1, B2, B6, niacin, and/or folic acid content than traditional hexaploid oat varieties.

TABLE 11

Vitamin B profile

| Sample | Vit. B1 (mg/100 g) | Vit. B2 (mg/100 g) | Vit. B6 (mg/100 g) | Niacin (mg/100 g) | Folic Acid (µg/100 g) |
|---|---|---|---|---|---|
| Hexaploid control | 0.64 | 0.12 | 0.11 | 1.13 | 32.82 |
| Tetraploid line 96.5.6 | 0.79 | 0.15 | 0.15 | —* | 78.14 |
| Tetraploid line 96.5.34 | 0.77 | 0.14 | 0.18 | 1.24 | 64.96 |
| Tetraploid line 100.2.235 | 0.89 | 0.16 | 0.19 | —* | 45.85 |

*not measured

Digestibility

Protein digestibility of *A. magna* ssp *domestica* was compared to traditional hexaploid oats. Briefly, a group of Sprague-Dawley derived, albino male rats was received from Harlan Laboratories, Inc. The animals were singly housed in suspended stainless steel perforated bottom caging. Litter paper was placed beneath the cages and was changed at least three times per week. The animal room was temperature controlled and had a 12-hour light/dark cycle. During a 2-day acclimation period, they were fed Harlan Teklad Global 16% Protein Rodent Diet® #2016 and filtered tap water was supplied ad libitum throughout the study.

Following acclimation to the laboratory, 16 male rats were selected for test on the basis of good health and body weight (58.9-71.7 grams). Four rats were assigned to each group as provided in Table 12.

TABLE 12

| Group No. | Product ID |
|---|---|
| 1 | Positive Control (Casein) |
| 2 | Endogenous Control (Protein Free)[1] |
| 3 | Traditional hexaploid Oats |
| 4 | *A. magna* ssp *domestica* |

[1]Protein - 0.79% (N × 6.25)

The test diets and the positive control (casein) diet were formulated to contain 10% protein (N×6.25) and levels of vitamins, minerals and calories to satisfy the requirements of the rats. The endogenous control (protein free) diet was formulated to contain the same levels of all nutrients except protein (e.g., protein was replaced with cornstarch). Each rat was provided with 15 grams per day of their respective diets for a total of 9 days.

Body weights were recorded at test initiation and at the start (Day 5) and end (Day 9) of the fecal collection period. Diet consumption was measured daily. Feces were collected daily at 24-hour intervals for the last five days of the study. At the end of the 5-day collection period, the feces of each animal were composited, dried and analyzed for nitrogen content.

True Digestibility was calculated as follows:

$$TD = \frac{I - (F - Fk) \times 100}{I}$$

TD=true digestibility; I=intake of dietary nitrogen (g) for test or casein control groups; F=fecal nitrogen (g) from the test or casein control groups; Fk=metabolic (endogenous) fecal nitrogen from the protein free group. Fk is calculated as follows:

$$Fk = \text{fecal nitrogen of protein free group } (g) \times \frac{I \text{ from Test Group}}{I \text{ from Protein Free Group}}$$

Protein Digestibility Corrected Amino Acid Score (PDCAAS) was calculated as follows: PDCAAS=(Amino Acid Score)×(True Protein Digestibility)

The amino acid score was determined in accordance with FAO Guidelines for Protein Quality Evaluation, 1990.

Amino Acid Analysis was conducted using Ion-exchange chromatography.

Tables 13-15 show the results of the digestibility study.

TABLE 13

PROTEIN DIGESTIBILITY CORRECTED AMINO

| Product ID | True Digestibility | Amino Acid Score | PDCAAS[1] |
|---|---|---|---|
| Casein Control | 97.005 | 1.23 | 119.316 |
| Hexaploid Oats | 92.371 | 0.578 | 53.390 |
| *A. magna* ssp *domestica* | 95.749 | 0.530 | 50.747 |

[1]In keeping with published recommendations the PDCAAS value for Casein is truncated to 100%

TABLE 14

DIET CONSUMPTION

| Group | Average Diet Consumption[1] (g) | Measured Protein Concentration in Prepared Diet | Average Protein Consumption[2] (g) | Average Intake of Dietary Nitrogen[3] |
|---|---|---|---|---|
| 1 | 63.2 | 10.28 | 6.497 | 1.04 |
| 2 | 29.0 | 0.79 | 0.229 | 0.037 |
| 3 | 64.4 | 10.11 | 6.511 | 1.042 |
| 4 | 66.2 | 10.63 | 7.037 | 1.126 |

[1]Consumption during the 5 day fecal collection period
[2](Average Diet Consumption × Measured Protein Concentration)/100
[3]Average Protein Consumption/6.25

TABLE 15

FECAL NITROGEN

| Group No | Average Total Fecal Excretion (g) | Nitrogen Present in Feces (%) | Average Total Nitrogen Excretion (g) |
|---|---|---|---|
| 1 | 4.9 | 1.86 | 0.090 |
| 2 | 2.2 | 1.26 | 0.027 |
| 3 | 6.6 | 2.15 | 0.141 |
| 4 | 5.7 | 1.94 | 0.110 |

Example 3—Tetraploid Oat Line Genetics

Genotypic relationship of tetraploid oat lines to *A. sativa* varieties and wild type *A. magna*, *A. moroccana*, *A. murphyii*, and *A. strigosa* accessions was compared based on allele sharing and hierarchical clustering using the following materials and methods.

Genotyping.

DNA from leaf tissue was extracted using the Qiagen DNeasy 96 Plant Kit (Qiagen, Hilden) and quantified using PicoGreen (LifeTechnologies, Carlsbad). After DNA quantification and normalization to 20 ng/µL, samples were prepared for sequencing using a modified double-restriction enzyme digestion protocol (Poland et al., 2012, *PLoS ONE*, 7.2:e32253). In brief, total genomic DNA (100 ng) was digested with 5 U of PstI-HF and MspI endonucleases (New England Biolabs, Ipswich) in a 10×NEB CutSmart buffer (1× final concentration). Thermocycler conditions for digestion were 34° C. for 120 minutes followed by 65° C. for 20 minutes. The restricted DNA was then ligated to forward adapters designed with a PstI overhang (M=0.00333 µM) and reverse Y-adapters (M=0.5 µM) with an MspI overhang. The forward adapters contained in-line barcode sequences which enable sample deconvolution after sequencing. Ligation was performed at 19° C. for 120 minutes followed by 65° C. for 20 minutes using a buffer containing 100 cohesive end units of T4 DNA ligase (New England Biolabs, Ipswich) and 10×NEB T4 Ligase Buffer (1× final). Following ligation, samples were pooled and PCR-amplified at 95° C. for 30 seconds; 16 cycles of 95° C. for 30 seconds, 62° C. for 20 seconds, 68° C. for 1 minute 30 seconds; and a final extension step at 72° C. for 5 minutes. The libraries were cleaned up using the QIAquick PCR Purification Kit (QIAGEN, Venlo) and verified using the Experion 1K DNA chip (BioRad, Hercules).

The library was pooled with additional sample libraries (n=192) and sequenced using one Illumina HiSeq2500 lane at the David H. Murdock Research Institute in Kannapolis, N.C. The UNEAK pipeline (Lu et al., 2013, *PLoS Genet*, 9:e100315) of the TASSEL 3.0 standalone software package (Bradbury et al., 2007, *Bioinformatics*, 23:2633-5) was used to analyze the FASTQ sequencing data and call sequence variants. The UNEAK pipeline does not require a reference genome and calls genotypes from alignment of sequence tag pairs. Parameters include a minimum sequence count of 5, the default error tolerance rate of 0.03, a minimum minor allele frequency of 0.02, a default maximum minor allele frequency of 0.5, and no limitation on the number of individuals covered by a sequence tag.

Although there is no reference genome for oat, there is an oat consensus map of hexaploid oat using EST-based and genomic-based markers (Oliver et al., 2013, *PLoS ONE*, 8(3):e58068; Huang et al., 2014, *PLoS ONE*, 9(7):e102448; and Tinker et al., 2014, *The Plant Genome*, 7:3). To obtain physical positions of sequence tags called by the UNEAK pipeline, the FASTA sequences of mapped markers were indexed using Bowtie v 1.1.1 (Langmead et al., 2009, *Genome Biol*, 10(3):R25). The FASTA sequence of the UNEAK tag pairs was aligned to mapped markers allowing for 2 mismatches in the local alignment. 3.07% of tag sequences aligned to previously mapped markers, representing 6,096 alignments. The positions of these tags were merged with the genotype call file (HapMap) output from the UNEAK pipeline. Genotypes were re-coded using custom scripts (homozygous allele 1=0; homozygous allele 2=2; heterozygous=1).

Statistical Analyses.

A single genotype matrix was developed for each of the oat species (*Avena sativa*=common hexaploid; *A. magna*, *A. maroccana*, and *A. murphyii*=tetraploid, and *A. strigosa*=diploid oat). Marker properties for each individual genotype matrix were evaluated for minor allele frequency (MAF) and proportion of missing genotypes. Markers with a MAF≤0.01 and ≥30% missing genotypes were removed. The cleaned data matrices were then used to evaluate genetic relationships between lines within a species. A kinship analyses was used to build an allele sharing covariate matrix. The overall matrix was then clustered using Ward's minimum variance method (Ward, 1963, *J Am Stat Assoc*, 55:236-44) to visualized the genetic relationships.

To evaluate the relationship between common oat (*A. sativa*) and tetraploid oat (*A. magna* and *A. maroccana*), a combined genotypic matrix was developed using shared markers from each of the species-specific cleaned genotype matrices. The combined matrix contained 10,776 loci that were shared between species. Of the remaining loci, 20,654 loci were unique to *A. sativa* and 1,382 were unique to *A. magna*. Table 16 provides 15 markers, each with 2 alleles, that were found in *A. magna*, including each of the tetraploid oat lines in FIG. 5, but not in *A. sativa*.

TABLE 16

| Marker designation | Allele 1 | Allele 2 |
|---|---|---|
| TP41002 | TGCAGTCCAAGATATTTAATGG GGAAGTGTGCAATATCGCAGC CAAACAGGGACTTCACCCTCT (SEQ ID NO: 1) | TGCAGTCCAAGATATTTAATGG GGAAGTGTGCAATATCGCAGC CAAACAGGGACTTCATCCTCT (SEQ ID NO: 2) |
| TP34748 | TGCAGGGCTTGCCTGAACATCC CAGAACCGCAGGGCACACCTA TGGCTTCGGCACACGCCGCCA (SEQ ID NO: 3) | TGCAGGGCTTGCCTGAACATCC CAGAACCGCGGGGCACACCTA TGGCTTCGGCACACGCCGCCA (SEQ ID NO: 4) |
| TP13061 | TGCAGCAGCTCGAGGCGGACA TGTCAATGTCGTGCTCCGAGAT | TGCAGCAGCTCGTGGCGGACA TGTCAATGTCGTGCTCCGAGAT |

TABLE 16-continued

| Marker designation | Allele 1 | Allele 2 |
|---|---|---|
| | CGGAAGAGCGGTTCAGCAGGA (SEQ ID NO: 5) | CGGAAGAGCGGTTCAGCAGGA (SEQ ID NO: 6) |
| TP22611 | TGCAGCGTTGGACACTAAAGG AGATACAGTTGTGAATGCTAA TAAGAAAAGTGCAGCTTCCAT C (SEQ ID NO: 7) | TGCAGCGTTGGACAGTAAAGG AGATACAGTTGTGAATGCTAA TAAGAAAAGTGCAGCTTCCAT C (SEQ ID NO: 8) |
| TP30271 | TGCAGGATCGCCACGTCGACG GTCTCCGCCATGGACCGCACC GAGATCGGAAGAGCGGTTCAG C (SEQ ID NO: 9) | TGCAGGCTCGCCACGTCGACG GTCTCCGCCATGGACCGCACC GAGATCGGAAGAGCGGTTCAG C (SEQ ID NO: 10) |
| TP21432 | TGCAGCGGCTCGACATCAGTG ACAACGAGCTCTCTGGCGCATT CCCCGCCAACGTGTCTCTCCC (SEQ ID NO: 11) | TGCAGCGGCTCGACATCAGTG ACAACGAGCTCTCTGGCGCGTT CCCCGCCAACGTGTCTCTCCC (SEQ ID NO: 12) |
| TP36725 | TGCAGGTCGAACCGCAGCGGG AACTCGTAGTCGGCATCACAC ACCATCTCCCAGCTCCGCATCA (SEQ ID NO: 13) | TGCAGGTCGAACCGCAGCGGG AACTCGTAGTCGGCGTCACAC ACCATCTCCCAGCTCCGCATCA (SEQ ID NO: 14) |
| TP15998 | TGCAGCCATGCCCGCCGCGAA TGCAAACGGGAATCACAGATT CCAATCAACAAACCAGAGAAA T (SEQ ID NO: 15) | TGCAGCCATGCCCGCCGCGAA TGCAAACGGGAATCACAGATT CCAATCAACAAACCAGAGCAA T (SEQ ID NO: 16) |
| TP1797 | TGCAGAAGCACCGCAGCAAGC AAGCTTCGCTAATGCTTACGCT CGGATCGGATGAGGCCAAGCA (SEQ ID NO: 17) | TGCAGAAGCACCGCAGCAAGC AAGCTTCGCTAATGCTTACGGT CGGATCGGATGAGGCCAAGCA (SEQ ID NO: 18) |
| TP28663 | TGCAGGACCTCGACCTCAGCG CCAACTACCTCTACGGCGCCGT CCCGAGATCGGAAGAGCGGTT (SEQ ID NO: 19) | TGCAGGACCTCGACCTCGGCG CCAACTACCTCTACGGCGCCGT CCCGAGATCGGAAGAGCGGTT (SEQ ID NO: 20) |
| TP3032 | TGCAGACACAAAGGCATGGGT ACGACGAGCCCCGACAGCAAC CGCACGTCCGCATGGAGGGTA C (SEQ ID NO: 21) | TGCAGACACAAAGGCATGGGT ACGACGAGCCTCGACAGCAAC CGCACGTCCGCATGGAGGGTA C (SEQ ID NO: 22) |
| TP44513 | TGCAGTTAGGTAGCACAGCTA GCTGTTCTTATTTTGCCCAACA CTTTTTTCTATTGGCCGAGAT (SEQ ID NO: 23) | TGCAGTTAGGTAGCACAGCTA GCTGTTCTTATTTTGCCCAACA TTTTTTTCTATTGGCCGAGAT (SEQ ID NO: 24) |
| TP46645 | TGCAGTTTTGGAGAATATTTCA GTTTTCAAAACCACAGTATTTA TTGCATACAAATACCTCAAA (SEQ ID NO: 25) | TGCAGTTTTGGAGAATATTTCA GTTTTCAAAACCACAGTATTTA TTGCATCCAAATACCTCAAA (SEQ ID NO: 26) |
| TP11161 | TGCAGCACCAGCAGCACCACC AGCTGGACGAGACGCAGCAGA GCTGGCTGCTCGGCCCGCCGA G (SEQ ID NO: 27) | TGCAGCACCAGCAGCACCACC AGCTGGACGAGACGCAGCAGA GCTGGCTGCTGGGCCCGCCGA G (SEQ ID NO: 28) |
| TP1999 | TGCAGAAGGACAGGCTACGTG ACTTAACAAACAAGGGATGCA ACTTGTTACCTTGATTGAACTT (SEQ ID NO: 29) | TGCAGAAGGACAGGCTACGTG GCTTAACAAACAAGGGATGCA ACTTGTTACCTTGATTGAACTT (SEQ ID NO: 30) |

A kinship analyses based on allele sharing and hierarchical clustering using the Ward's minimum variance method were used to evaluate the overall genetic relationships between and within both species as preciously described.

Results.

Figure 5:
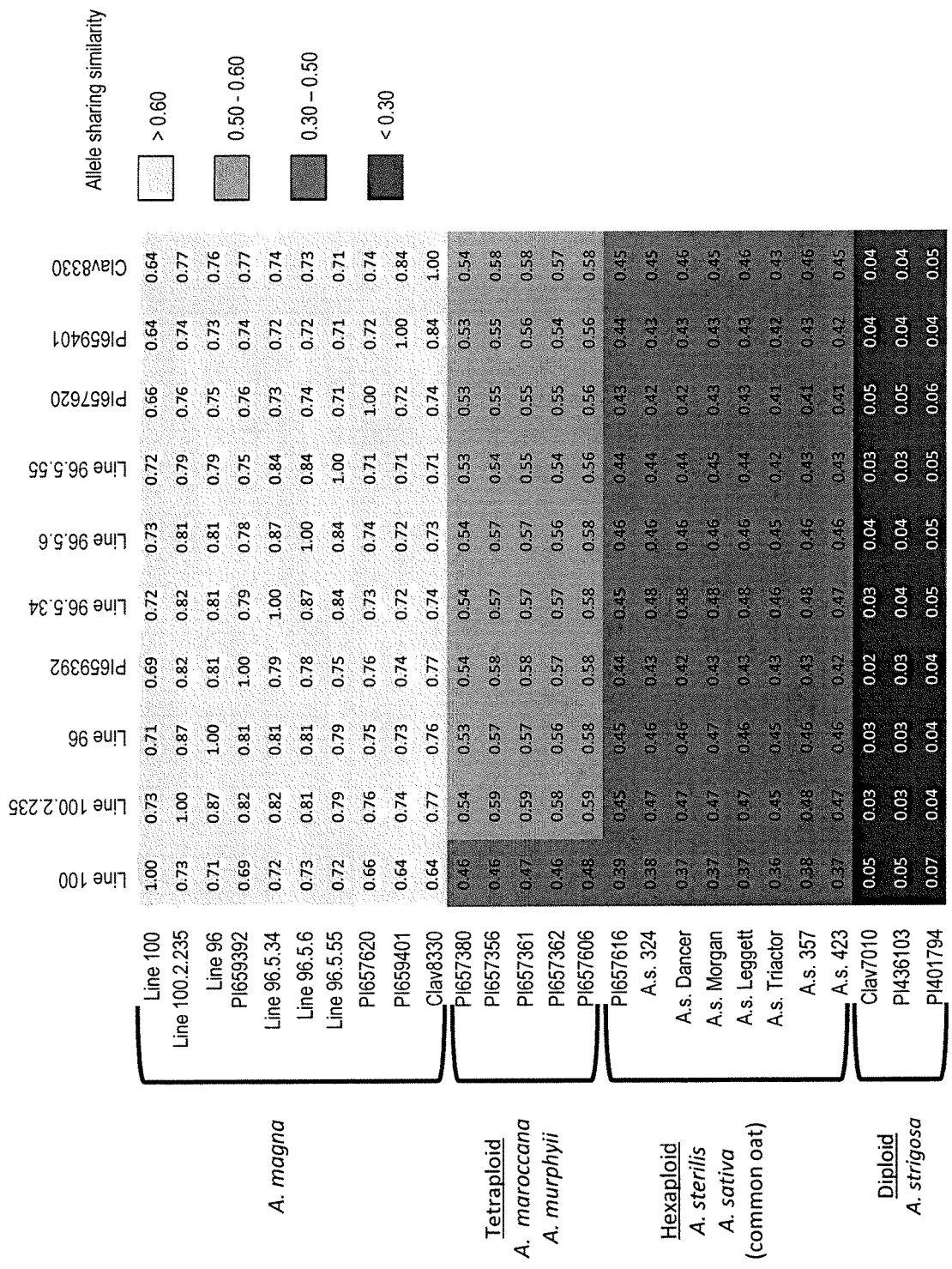
FIG. 5 is an allele sharing similarity matrix comparing allele sharing similarity between *A. magna* ssp *domestica* lines (Line 100, Line 100.235, Line 96, Line 96.5.34, Line 96.5.6, Line 96.5.55), wild *A. magna* accessions (PI659392, PI657620, PI659401, Clav8330), an *A. maroccana* accession (PI657380), *A. murphyii* accessions (PI657356, PI657361, PI657362, PI657606), an *A. sterilis* accession (PI657616), common hexaploid oat lines (A.s. 324, A.s. Dancer, A.s. Morgan, A.s. Leggett, A.s. Triactor, A.s. 357, A.s. 423), and *A. strigosa* accessions (Clav7010, PI436103, PI401794). All *A. magna* lines and accessions had greater than 60% allele sharing similarity (i.e., >0.60) with each other, while hexaploid lines and accessions (*A. sterilis* and *A. sativa*) and diploid accessions (*A. strigosa*) had less than 50% allele sharing similarity (i.e., <0.50) with any of the *A. magna* lines and accessions.

FIG. 5 shows the results of genetic marker Global variance based on over 12,000 different loci. From the figure, you can see that there is variation that is specific to *A. magna* ssp *domestica* lines, *Avena maroccana* lines as well as *Avena sativa* (common oat hexaploid) and *Avena murphyi* (tetraploid), and *Avena strigosa* (dipolid) which can differentiate between the different species and varieties.

Tetraploid oat lines 100, 100.2.235, 96, 96.5.34, 96.5.6, and 96.5.55 have greater than 60% allele sharing similarity with each other and with each of the tested wild *A. magna* accessions. The similarity between each line and the wild *A. magna* accessions was similar to the similarity between each of the wild *A. magna* accessions. In addition, tetraploid oat accessions of *A. maroccana* and *A. murphyii* species had greater than 50% allele sharing similarity to tetraploid oat lines 100.2.235, 96, 96.5.34, 96.5.6, and 96.5.55. In contrast, the traditional hexaploid oat varieties and the hexaploid *A. sterilis* accession had less than 50% allele sharing similarity to the tetraploid oat lines. Diploid *A. strigosa* accessions had less than 10% allele sharing similarity to any of the tetraploid oat lines.

DEPOSIT STATEMENT

A deposit of seed of oat varieties 96.5.6, 96.5.34, and 100.2.235 disclosed herein, is and has been maintained by Applicant General Mills (One General Mills Blvd, Minneapolis, Minn. 55426) since prior to the filing date of this application. A deposit of at least 2500 seeds of each variety or line has also been submitted under the Budapest Treaty to the American Type Culture Collection (ATCC), Rockville, Md., 20852. Certificates of Deposit were granted on Oct. 12, 2015, for oat variety 96.5.6 as ATCC designation PTA-122534, oat variety 96.5.34 as ATCC designation PTA-122532, and oat variety 100.2.235 as ATCC designation PTA-122533. Applicant will meet all the requirements of 37 C.F.R. §§ 1.801-1.809 and the Budapest Treaty.

What is claimed is:

1. An *Avena magna* variety selected from variety 96.5.6 (American Type Culture Collection accession PTA-122534), 96.5.34 (American Type Culture Collection accession PTA-122532), and 100.2.235 (American Type Culture Collection accession PTA-122533).

2. A tetraploid oat variety essentially derived from tetraploid oat variety 96.5.34 (American Type Culture Collection accession PTA-122532), 96.5.6 (American Type Culture Collection accession PTA-122534), or 100.2.235 (American Type Culture Collection accession PTA-122533).

3. An *Avena magna* variety that includes the following traits that are inherited from one or more of an *Avena magna* variety selected from 96.5.6 (American Type Culture Collection accession PTA-122534), 96.5.34 (American Type Culture Collection accession PTA-122532), and 100.2.235 (American Type Culture Collection accession PTA-122533):
 a. a statistically significant increase in seed protein content as compared to *Avena sativa* variety 'Leggett' when grown under the same environment under the same conditions, and
 b. a semi-dwarf height.

* * * * *